(12) United States Patent
Lawson et al.

(10) Patent No.: US 10,048,253 B2
(45) Date of Patent: Aug. 14, 2018

(54) METHOD FOR IDENTIFYING COMPOUNDS OF THERAPEUTIC INTEREST

(71) Applicant: UCB PHARMA S.A., Brussels (BE)

(72) Inventors: Alastair David Griffiths Lawson, Slough (GB); Alistair James Henry, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 695 days.

(21) Appl. No.: 14/409,424

(22) PCT Filed: Jun. 28, 2013

(86) PCT No.: PCT/EP2013/063747
§ 371 (c)(1),
(2) Date: Dec. 18, 2014

(87) PCT Pub. No.: WO2014/001557
PCT Pub. Date: Jan. 3, 2014

(65) Prior Publication Data
US 2015/0219635 A1 Aug. 6, 2015

Related U.S. Application Data
(60) Provisional application No. 61/849,830, filed on Jun. 28, 2012.

(51) Int. Cl.
*G01N 33/53* (2006.01)
*G01N 33/542* (2006.01)
(Continued)

(52) U.S. Cl.
CPC ..... *G01N 33/5308* (2013.01); *C07K 16/4291* (2013.01); *G01N 33/542* (2013.01);
(Continued)

(58) Field of Classification Search
None
See application file for complete search history.

(56) References Cited

U.S. PATENT DOCUMENTS 5,223,409 A 12/1993 Ladner et al.
5,403,484 A 4/1995 Ladner et al.
(Continued)

FOREIGN PATENT DOCUMENTS

EP 0438474 7/1991
EP 0463151 1/1992
(Continued)

OTHER PUBLICATIONS

Holdom et al., "Conformational changes in IgE contribute to its uniquely slow dissociation rate from receptor FcεRI," Nat. Struct. Mol. Biol. 2011, 18:571-576, published online Apr. 24, 2011.*
(Continued)

*Primary Examiner* — Kaijiang Zhang
(74) *Attorney, Agent, or Firm* — McDonnell Boehnen Hulbert & Berghoff LLP

(57) ABSTRACT

The present invention relates to an improved method for drug discovery. In particular the present invention provides a method of identifying compounds capable of binding to a functional conformational state of a protein of interest or protein fragment thereof, said method comprising the steps of: (a) Binding a function-modifying antibody to the target protein of interest or a fragment thereof to provide an antibody-constrained protein or fragment, wherein the antibody has binding kinetics with the protein or fragment which are such that it has a low dissociation rate constant, (b) Providing a test compound which has a low molecular weight, (c) Evaluating whether the test compound of step b) binds the antibody constrained protein or fragment, and (d)
(Continued)

Figure 1:
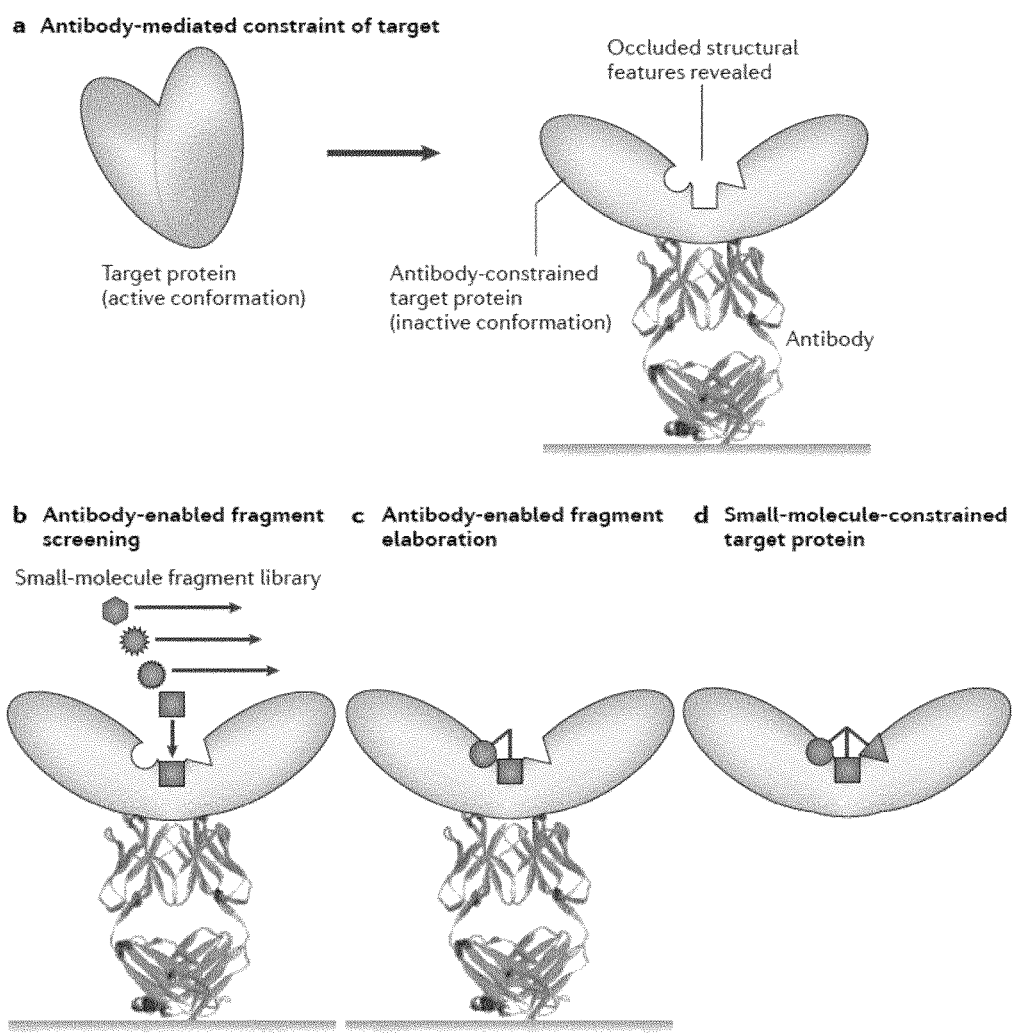

Select a compound from step c) based on the ability to bind to the protein or fragment thereof.

23 Claims, 16 Drawing Sheets

(51) Int. Cl.
  *C40B 30/04* (2006.01)
  *C07K 16/42* (2006.01)
  *G06F 19/16* (2011.01)
(52) U.S. Cl.
  CPC .......... *G06F 19/16* (2013.01); *C07K 2299/00* (2013.01); *C07K 2317/55* (2013.01); *C07K 2317/76* (2013.01); *C07K 2317/92* (2013.01); *C40B 30/04* (2013.01); *G01N 2500/02* (2013.01); *G01N 2500/04* (2013.01); *G01N 2500/20* (2013.01)

(56) References Cited

U.S. PATENT DOCUMENTS

| | | | |
|---|---|---|---|
| 5,427,908 | A | 6/1995 | Dower et al. |
| 5,516,637 | A | 5/1996 | Huang et al. |
| 5,545,806 | A | 8/1996 | Londberg et al. |
| 5,569,825 | A | 10/1996 | Londberg et al. |
| 5,571,698 | A | 11/1996 | Ladner et al. |
| 5,580,717 | A | 12/1996 | Dower et al. |
| 5,585,089 | A | 12/1996 | Queen et al. |
| 5,625,126 | A | 4/1997 | Londberg et al. |
| 5,633,425 | A | 5/1997 | Londberg et al. |
| 5,658,727 | A | 8/1997 | Barbas et al. |
| 5,661,016 | A | 8/1997 | Londberg et al. |
| 5,698,426 | A | 12/1997 | Huse |
| 5,733,743 | A | 3/1998 | Johnson et al. |
| 5,750,753 | A | 5/1998 | Kimae et al. |
| 5,770,429 | A | 6/1998 | Londberg et al. |
| 5,780,225 | A | 7/1998 | Wigler et al. |
| 5,821,047 | A | 10/1998 | Garrard et al. |
| 5,969,108 | A | 10/1999 | McCafferty et al. |

FOREIGN PATENT DOCUMENTS

| | | |
|---|---|---|
| EP | 0546073 | 6/1993 |
| WO | WO 90/02809 | 3/1990 |
| WO | WO 91/09967 | 7/1991 |
| WO | WO 91/10737 | 7/1991 |
| WO | WO 92/01047 | 1/1992 |
| WO | WO 92/02551 | 2/1992 |
| WO | WO 92/18619 | 10/1992 |
| WO | WO 92/22853 | 12/1992 |
| WO | WO 93/11236 | 6/1993 |
| WO | WO 95/15982 | 6/1995 |
| WO | WO 95/20401 | 8/1995 |
| WO | WO 2007/011392 | 1/1997 |
| WO | WO 97/16177 | 5/1997 |
| WO | WO 97/049805 | 12/1997 |
| WO | WO 97049805 | 12/1997 |
| WO | WO 03/050531 | 6/2003 |
| WO | WO2004/051268 | 6/2004 |
| WO | WO 2004/106377 | 12/2004 |
| WO | WO 2005/003169 | 1/2005 |
| WO | WO 2005/003170 | 1/2005 |
| WO | WO 2005/003171 | 1/2005 |
| WO | WO 05/113605 | 12/2005 |
| WO | WO 2012/007593 A1 | 1/2012 |
| WO | WO 2012/007594 A1 | 1/2012 |
| WO | WO 2012/175643 A2 | 12/2012 |

OTHER PUBLICATIONS

Holdom et al., "Conformational changes in IgE contribute to its uniquely slow dissociation rate from receptor FcεRI," Nat. Struct. Mol. Biol. 2011, 18:571-576, with one page of supplemental "Online Methods", published online Apr. 24, 2011.*

Szczepankiewicz et al. (2003) Journal of the American Chemical Society, 125(14), 4087-4096.

Raimundo et al. (2004) Journal of Medicinal Chemistry 47(12), 3111-3130.

Braisted et al. (2003) Journal of the American Chemical Society 125(13), 3714-3715.

Huth et al. (2007) Chemical Biology & Drug Design 70(1), 1-12.

Petros et al. (2006),Journal of Medicinal Chemistry 49(2), 656-663.

Geschwindner et al. (2007) Journal of Medicinal Chemistry 50(24), 5903-5911.

Edwards et al. (2007) Journal of Medicinal Chemistry 50(24), 5912-5925.

Hubbard, et al. (2007) Current Topics in Medicinal Chemistry, 7(16), 1568-1581.

Gould, H.J. & Sutton, B.J. (2008) IgE in allergy and asthma today. Nature Reviews Immunology 8, 205-217.

Padlan, E.A. & Davies, (1986) D.R. A model of the Fc of Immunoglobulin-E. Molecular Immunology 23, 1063-1075.

Davis, K.G. Glennie, M. Harding, S.E. & Burton, D.R. (1990) A model for the solution conformation of rat IgE. Biochemical Society Transactions 18, 935-936.

Zheng Y. Shopes, B., Holowka, D. & Baird, B. (1991) Conformations of IgE bound to its receptor Fc-Epsilon-RI and in solution. Biochemistry 30, 9125-9132.

Beavil, A.J., Young, R.J., Sutton, B.J. & Perkins, S.J. (1995) Bent domain-structure of recombinant human IgE-Fc in solution by x-ray and neutron-scattering in conjunction with an automated curve-fitting procedure. Biochemistry 34, 14449-14461.

Van, T. et al., (2002), the crystal structure of IgE Fc reveals an asymmetrically bent conformation. Nature Immunology 3, 681-686.

Arkin M R et al, Small-molecule inhibitors of protein-protein interactions: progressing towards the dream, Nature Reviews. Drug Discovery, Apr. 1, 2004, pp. 301-317: box 5; conclusions; abstract, vol. 3 No. 4, Nature Publishing Group.

McDonnell, J.M. et al. (2001) The structure of the IgE C epsilon 2 domain and its role in stabilizing the complex with its high-affinity receptor Fc epsilon RI alpha. Nature Structural Biology 8, 437-441.

Holgate, S.T., Djukanovic, R., Casale, T. & Bousquet, J. (2005) Anti-immunoglobulin E treatment with omalizumab in allergic diseases: an update on anti-inflammatory activity and clinical efficacy. Clinical and Experimental Allergy 35, 408-416.

Hunt, J. et al. (2012) A fluorescent biosensor reveals conformational changes in human Immunoglobulin E Fc: Implications for mechanisms of receptor binding, inhibition, and allergen recognition. The Journal of Biological Chemistry 287, 17459-70.

Wurzburg, B.A. & Jardetzky, T.S. (2009) Conformational flexibility in Immunoglobulin E-Fc(3-4) revealed in multiple crystal forms. Journal of Molecular Biology 393, 176-190.

Garman, S.C., Wurzburg, B.A., Tarchevskaya, S.S., Kinet, J.P. & Jardetzky, T.S. (2000) Structure of the Fc fragment of human IgE bound to its high-affinity receptor Fc epsilon RI alpha. Nature 406, 259-266.

Barducci, A., Bussi, G. & Parrinello, M. (2008) Well-tempered metadynamics: a smoothly converging and tunable free-energy method. Physical Review Letters 100, 020603-020603.

Crespo, Y., Marinelli, F., Pietrucci, F. & Laio, A. (2010) Metadynamics convergence law in a multidimensional system. Physical Review E 81.

Barducci, A., Bonomi, M. & Parrinello, M. (2011) Metadynamics. Wiley Interdisciplinary Reviews—Computational Molecular Science 1, 826-843.

Perkins, S.J., Nealis, A.S., Sutton, B.J. & Feinstein, (1991) A. Solution structure of human and mouse Immunoglobulin M by synchrotron X-ray scattering and molecular graphics modelling. A possible mechanism for complement activation. Journal of Molecular Biology 221, 1345-66.

Czajkowslcy, D.M. & Shao, Z. (2009) The human IgM pentamer is a mushroom-shaped molecule with a flexural bias. Proceedings of the National Academy of Sciences of the United States of America 106, 14960-5.

(56) References Cited

OTHER PUBLICATIONS

Tolar, P., Sohn, H.W., Liu, W. & Pierce, S.K. (2009) The molecular assembly and organization of signaling active B-cell receptor oligomers. Immunological Reviews 232, 34-41.
McCoy, A.J. et al. (2007) Phaser crystallographic software. Journal of Applied Crystallography 40, 658-674.
Schwarzenbacher, R., Godzik, A., Grzechnik, S.K. & Jaroszewski, L. (2004) The importance of alignment accuracy for molecular replacement. Acta Crystallographica Section D-Biological Crystallography 60, 1229-1236.
Stein, N. (2008) CHAINSAW: a program for mutating pdb files used as templates in molecular replacement. Journal of Applied Crystallography 41, 641-643.
Adams, P.D. et al. (2011) The Phenix software for automated determination of macromolecular structures. Methods 55, 94-106.
Murshudov, G.N. et al. (2011) REFMAC5 for the refinement of macromolecular crystal structures. Acta Crystallographica Section D—Biological Crystallography 67, 355-367.
Emsley, P., Lohkamp, B., Scott, W.G. & Cowtan, K. (2010) Features and development of Coot. Acta Crystallographica Section D—Biological Crystallography 66, 486-501.
Chen, V.B. et al. (2010) MolProbity: all-atom structure validation for macromolecular crystallography. Acta Crystallographica Section D—Biological Crystallography 66, 12-21.
Lutteke, T., Frank, M. & von der Lieth, C.W. (2005) Carbohydrate Structure Suite (CSS): analysis of carbohydrate 3D structures derived from the PDB. Nucleic Acids Research 33, D242-D246.
Krissinel, E. & Henrick, K. (2007) Inference of macromolecular assemblies from crystalline state. Journal of Molecular Biology 372, 774-797.
Bailey, S. (1994) The CCP4 suite—programs for protein crystallography. Acta Crystallographica Section D—Biological Crystallography 50, 760-763.
Hayward, S. & Berendsen, H.J.C. (1998) Systematic analysis of domain motions in proteins from conformational change: New results on citrate synthase and T4 lysozyme. Proteins—Structure Function and Genetics 30, 144-154.
Pettersen, E.F. et al. (2004) UCSF chimera—A visualization system for exploratory research and analysis. Journal of Computational Chemistry 25, 1605-1612.
Beomkyu Kim et al, A time-resolved fluorescence resonance entergy transfer assay suitable to high-throughput screening for inhibitors of immunoglobulin E-receptor interactions, Analytical Biochemistry, Dec. 1, 2012, pp. 84-89: the whole document, vol. 431 No. 2.
May L T et al, Allosteric modulation of G protein-coupled receptors, Current Pharmaceutical Deisgn, Jan. 1, 2004, pp. 2003-2013: the whole document, vol. 10 No. 17.
Wurzburg B A et al, Structure of the human IgE-Fc Cepsilon3-Cepsilon4 reveals conformational flexibility in the antibody effector domains, Immunity, Sep. 1, 2000, pp. 375-385: p. 383, para"biological and therapeutic mplications . . . flexibility", vol. 13 No. 3.
Horn and Shoichet (2004) Allosteric inhibition through core disruption. J. Mol. Biol. 336, 1283-1291.
Holliger and Hudson (2005) Nature Biotech. 23(9):1126-1136.
Adair and Lawson (2005) Drug esign Reviews—Online 2(3), 209-217).
Verma et al. (1998) Journal of Immunological Methods, 216, 165-181).
Nygren and Uhlen (1997) Current Opinion in Structural Biology, 7, 463-469.
Kohler & Milstein (1975) Nature, 256:495-497.
Kozbor et al. (1983) Immunology Today, 4:72.
Cole et al. (1985) Monoclonal Antibodies and Cancer Therapy, pp. 77-96, Alan R Liss, Inc.
Babcock, J. et al. (1996) Proc. Natl. Acad. Sci. USA 93(15):7843-7848.
Kashmiri et al. (2005) Methods, 36, 25-34.
Brinkman et al. (1995) in J. Immunol. Methods, 182: 41-50.
Ames et al. (1995) J. Immunol. Methods, 184:177-186.
Kettleborough et al. (1994) Eur. J. Immunol. 24:952-958.
Persic et al. (1997) Gene, 187 9-18.
Burton et al. (1994) Advances in Immunology, 57:191-280.
Hamers et al. (1993) Nature, 363, 446-448.
Muyldermans, et al. (2001) Trends. Biochem.Sci. 26, 230-235.
Decanniere, et al. (2000) J. Mol.Biol, 300, 83-91.
Nguyen et al. (2001) Adv. Immunol., 79, 261-296.
Lauwereys et al. (1998) EMBO J, 17, 3512-3520.
Desmyter et al. (1996) Nat.Struct.Biol.3, 803-811.
De Genst et al. (2006) PNAS, 103, 12, 4586-4591.
Stanfield et al. (2004) Science, 305, 1770-1773.
Liu et al. (2007) BMC Biotechnol., 7, 78.
Saerens et al. (2004) J. Biol. Chem., 279 (5), 51965-72.
Yang et al. (1995) J. Mol. Biol., 254, 392-403.
Marks et al. (1992) Bio/Technology, 10, 779-783.
Low et al. (1996) J. Mol. Biol., 250, 359-368.
Patten et al. (1997) Curr. Opin. Biotechnol., 8, 724-733.
Thompson et al. (1996) J. Mol. Biol., 256, 77-88.
Crameri et al. (1998) Nature, 391, 288-291.
Moreira et al. (2007) J Comput Chem. Feb 28(3):644-54.
Hajduk and Greer (2007) Nat. Rev. Drug. Discov. 6(3), 211-219.
Baurin et al. (2004) J. Chem. Inf. Comput. Sci, 44, 2157-2166.
Zartler and Shapiro (2005) Curr. Opin. Chem. Biol., 9, 366-370.
Rees et al. (2004) Nature Rev. Drug Discov. 3, 660-672.
Hartshorn et al. (2005) J. Med. Chem. 48, 403-413.
Shuker et al. (1996) Science 21A, 1531-1534.
Vanwetswinkel et al. (2005) Chemistry & Biology, 12(2): 207-216.
DeLano (2002) Curr. Opin. Struct. Biol. 12, 14-20.
Boehm et al. (2000) J. Med. Chem. 43, 2664-2674.
Lebowitz et al. (2002) Protein Sci. 11, 2067-2079.
Metz et al. (2003) Meth.Principles.Med.Chem, 19, 213-236.
Neumann et al. (2005) Lett. Drug. Des. Discovery, 2, 590-594.
Carbeck et al. (1998) Acc.Chem. Res. 31, 343-350.
Friesner et al. (2004) J Med Chem. Mar. 25;47(7):1739-49.
Jones et al. (1997) J Mol Biol. Apr. 4;267(3):727-48.
Lipinski et al. (1997) Adv. Drug.Del.Rev, 23, 3-25.
Hubbard et al. (2007) Curr. Opin. Drug Discov. Devel., 10, 289-297.

\* cited by examiner

Figure 3
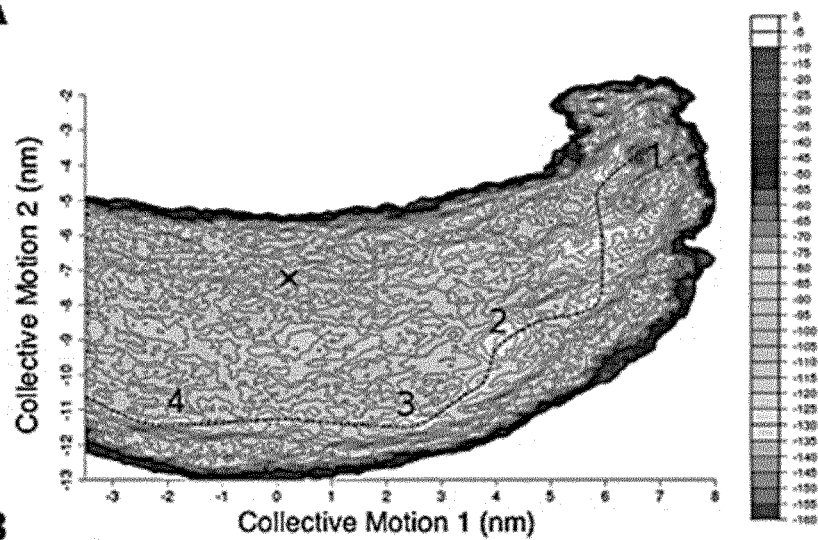
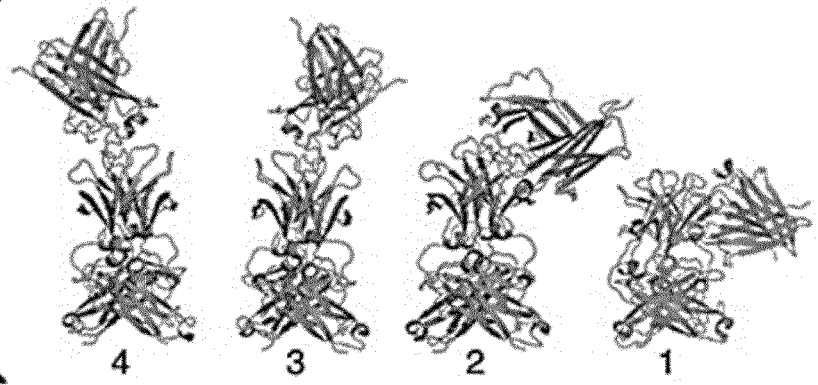
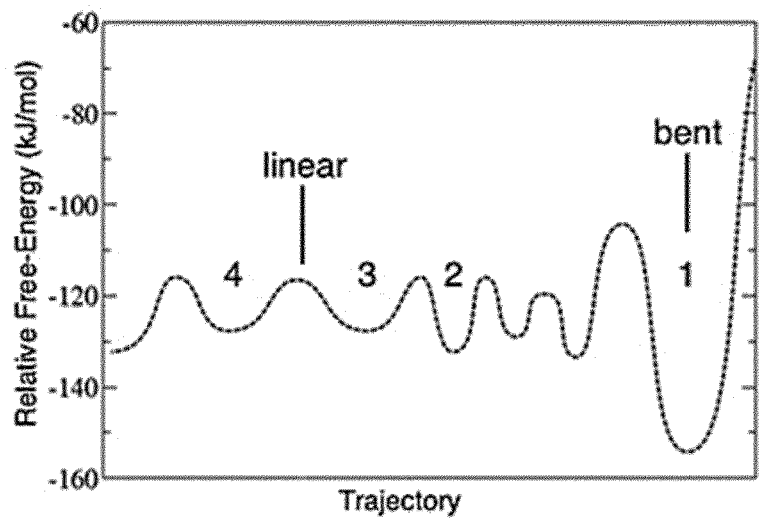

Figure 4a & b
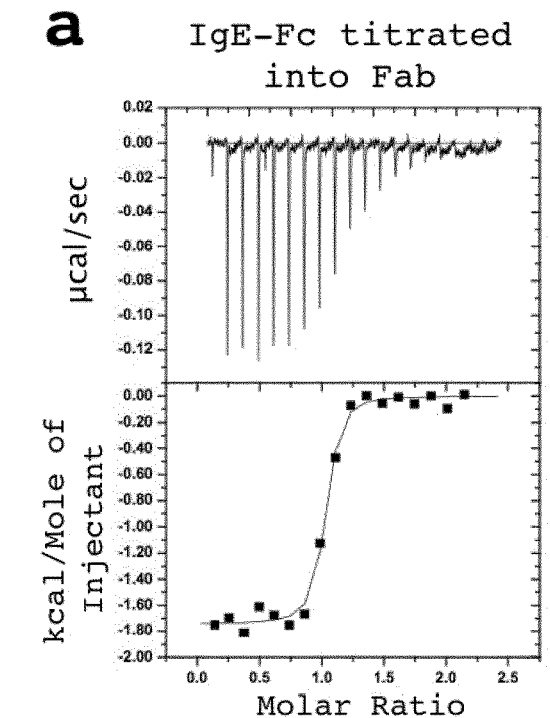
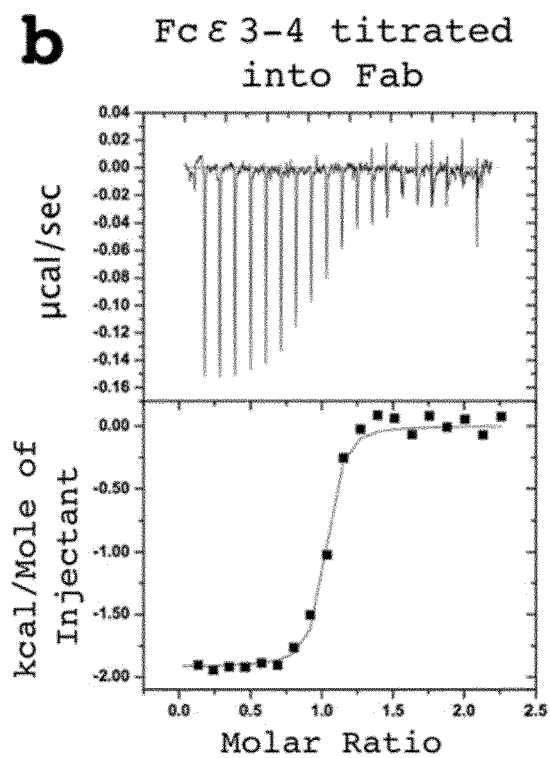

Figure 4c & d
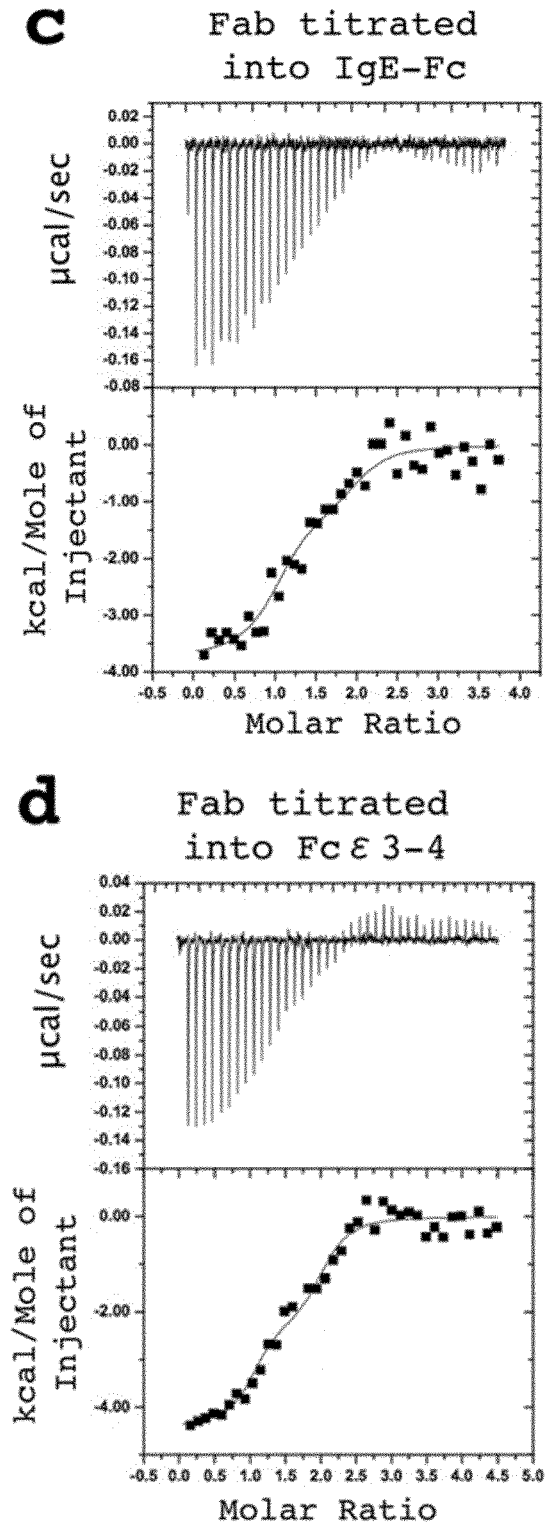

Figure 9
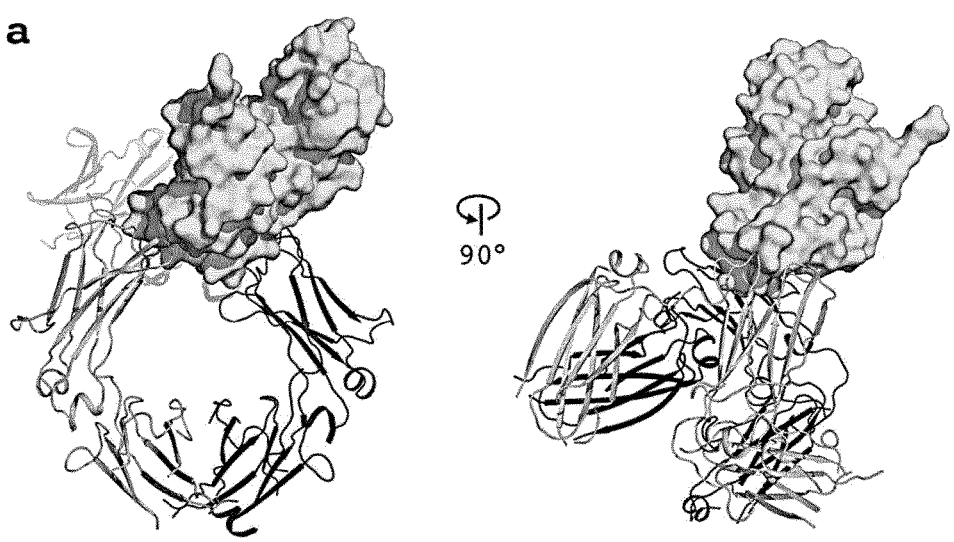
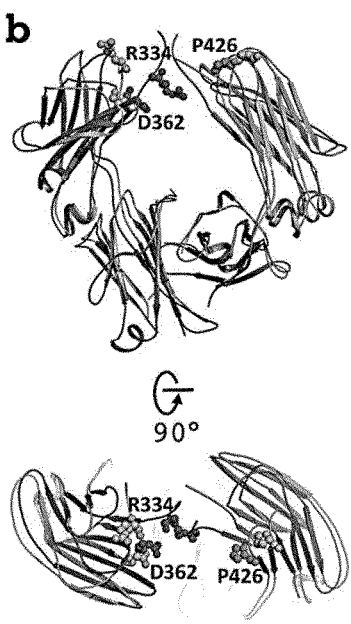
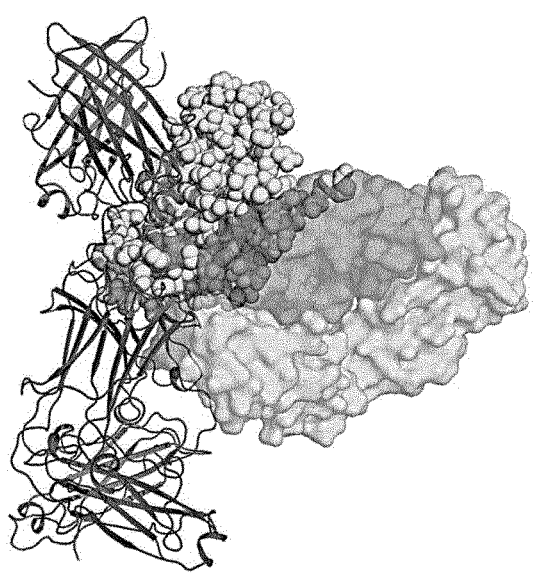

Figure 10
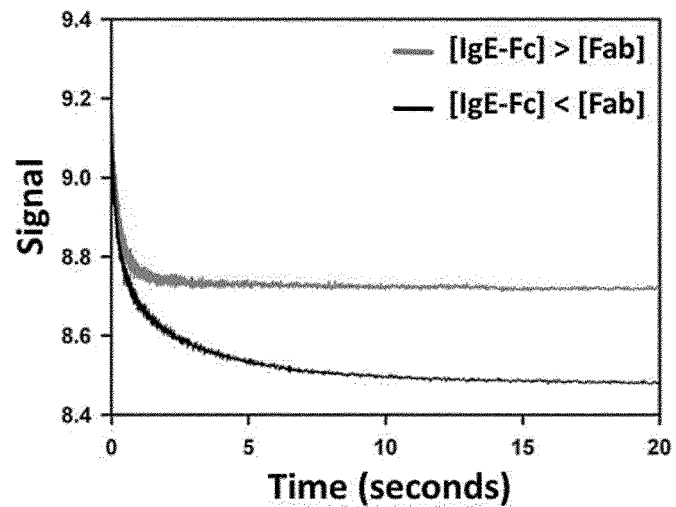
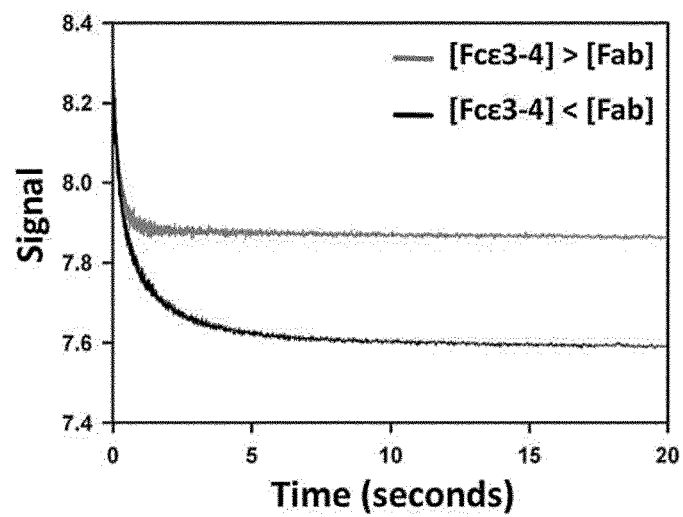

Figure 11a & b
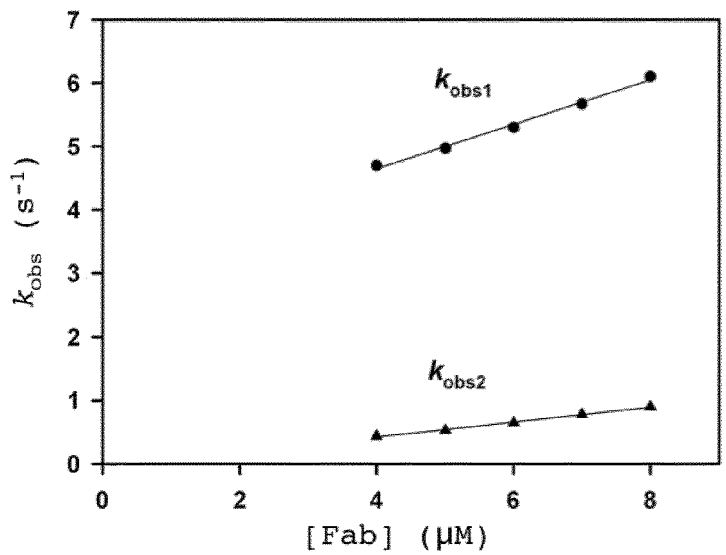
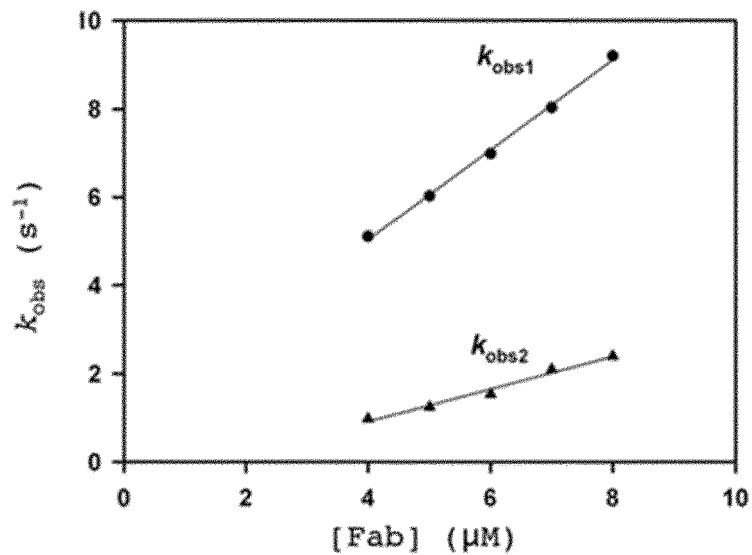

Figure 11c & d
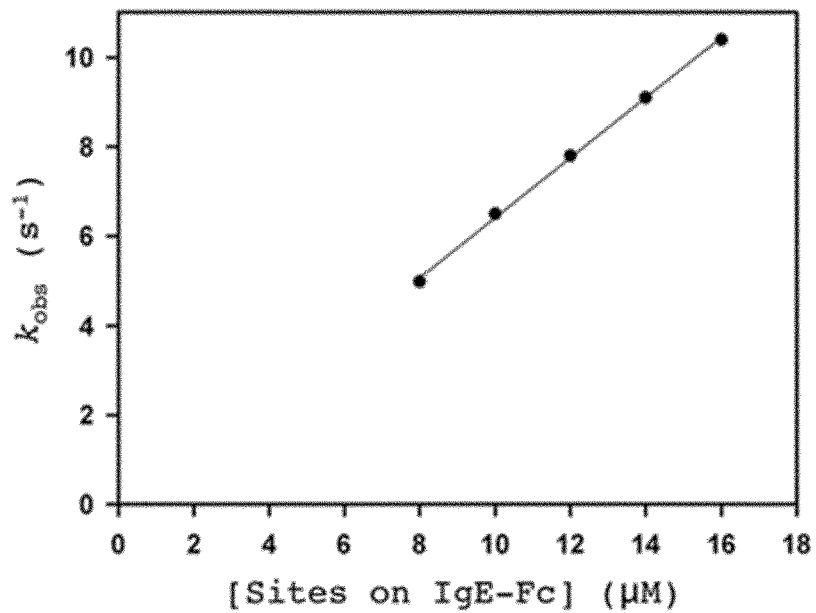
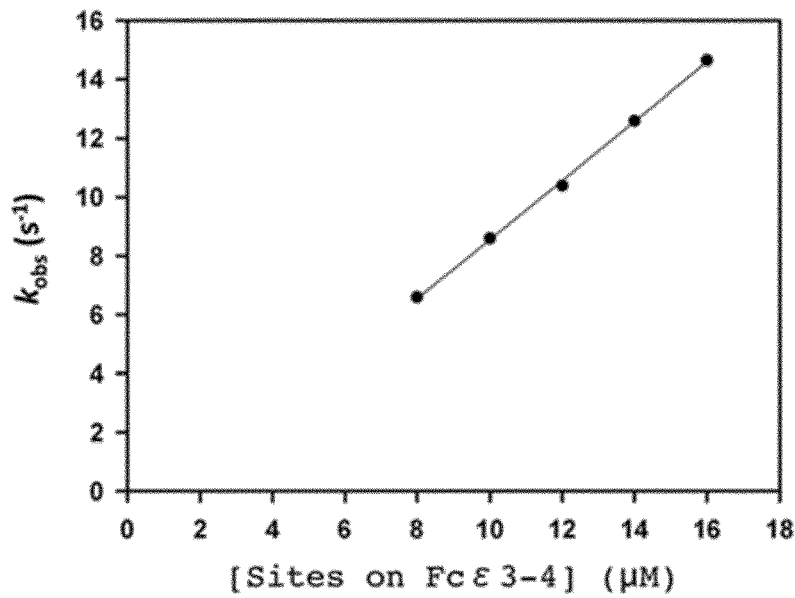

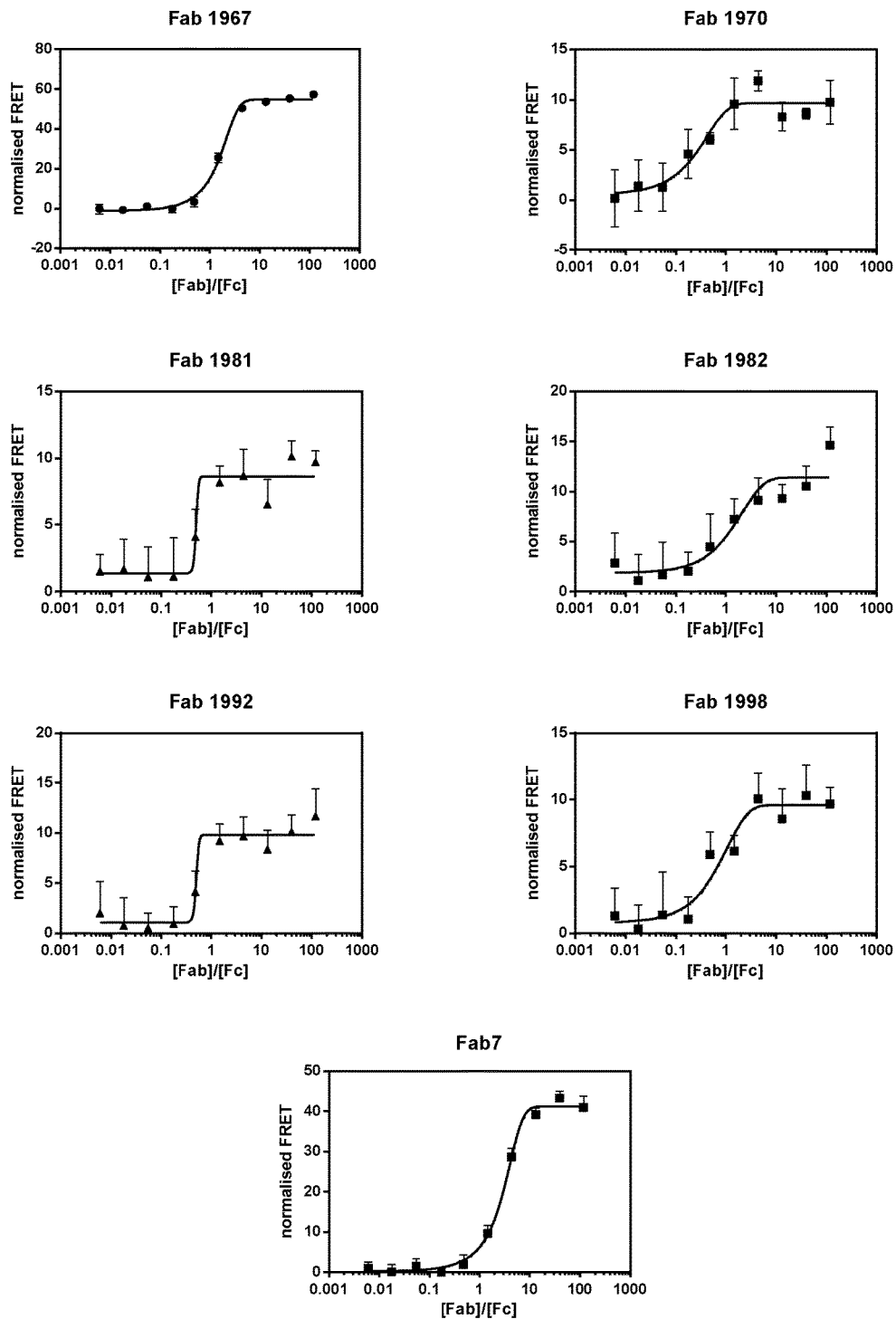
Figure 12    FRET analysis

Figure 14

FAB7 Heavy Chain Polynucleotide Sequence (seq id no:1)
ATGGAATGGATCTGGATATTTCTCTTCCTCCTGTCAGTAACTACAGGAGTCCATTCTCAGGTAC
AGCTGCAGCAGTCAGGTCCAGGACTGGTGAAGCCCTCGCAGACCCTCTCACTCACCTGTGGCAT
CTCCGGGGACAGTGTCTCTAGCAACAGTGCTGCTTGGAACTGGCTCAGGCAGTCCCCATCGAGA
GGCCTTGAGTGGCTGGGAAGAACATACTACAGGTCCAAGTGGTATAATGATTATGCAGTATCTA
TGAAGAGTCGAATAACCATCAACCCAGACACATCCAGGAACCAGTTCTCCCTGCAGTTGAATTC
TGTGACTCCCGAGGACACGGCTGTGTATTACTGTGCAAGGGATGGAGAAATAAGTTACGACTAC
TACTACTACGGTATGGACGTCTGGGGCCGCGGCACCCTGGTCACCGTCTCGAGCGCTTCTACAA
AGGGCCCATCGGTCTTCCCCCTGGCACCCTCCTCCAAGAGCACCTCTGGGGGCACAGCGGCCCT
GGGCTGCCTGGTCAAGGACTACTTCCCCGAACCGGTGACGGTGTCGTGGAACTCAGGCGCCCTG
ACCAGCGGCGTGCACACCTTCCCGGCTGTCCTACAGTCCTCAGGACTCTACTCCCTCAGCAGCG
TGGTGACCGTGCCCTCCAGCAGCTTGGGCACCCAGACCTACATCTGCAACGTGAATCACAAGCC
CAGCAACACCAAGGTGGACAAGAAAGTTGAGCCCAAATCTTGT FAB7 Heavy Chain Amino Acid Sequence (seq id no: 2)
*MEWIWIFLFLLSVTTGVHS*QVQLQQSGPGLVKPSQTLSLTCGISGDSVSSNSAAWNWLRQSPSR
GLEWLGRTYYRSKWYNDYAVSMKSRITINPDTSRNQFSLQLNSVTPEDTAVYYCARDGEISYDY
YYYGMDVWGRGTLVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPKSC.

FAB7 Light Chain Polynucleotide Sequence (seq id no: 3)
ATGGACTGGTCTCCTCTCCTCCTCACTCTCCTCGCTCACTGCACAGGGTCCTGGGCCCAGTCTG
TCCTGACGCAGCCGCCCTCAGCGTCTGGGACCCCCGGGCAGAGGGTCACCATCTCCTGTTCTGG
CAGCAGCTCCAACATCGGAAATAATGGTGTGAACTGGTACCAACAAGTCCCAGGAAAGCCTCCC
AAACTCCTCATCTATTATGATGATCTGCTGCCCTCAGGGGTCTCTGACCGATTCTCTGGCTCCA
AGTCTGGCACCTCAGCCTCCCTGGCCATCAGTGGGCTCCAGTCTGAGGATGAGGCTGATTATTA
CTGTGAAGCGTGGGATGACAGTCTGGATGGTGTGGTTTTCGGCGGAGGCACCAAGCTGACCGTC
CTAGGCCAGCCTAAGGCTGCACCCAGTGTCACTCTGTTCCCGCCCTCCTCTGAGGAGCTTCAAG
CCAACAAGGCCACACTGGTGTGTCTCATAAGTGACTTCTACCCGGGAGCCGTGACAGTGGCCTG
GAAGGCAGATAGCAGCCCCGTCAAGGCGGGAGTGGAGACCACCACACCCTCCAAACAAAGCAAC
AACAAGTACGCGGCCAGCAGCTACCTGAGCCTGACGCCTGAGCAGTGGAAGTCCCACAGAAGCT
ACAGCTGCCAGGTCACGCATGAAGGGAGCACCGTGGAGAAGACAGTGGCCCCTACAGAATGTTC
A FAB7 Light Chain Polynucleotide Sequence (seq id no: 4)
*MDWSPLLLTLLAHCTGSW*AQSVLTQPPSASGTPGQRVTISCSGSSSNIGNNGVNWYQQVPGKPP
KLLIYYDDLLPSGVSDRFSGSKSGTSASLAISGLQSEDEADYYCEAWDDSLDGVVFGGGTKLTV
LGQPKAAPSVTLFPPSSEELQANKATLVCLISDFYPGAVTVAWKADSSPVKAGVETTTPSKQSN
NKYAASSYLSLTPEQWKSHRSYSCQVTHEGSTVEKTVAPTECS.

SEQUENCE LISTING

<160> NUMBER OF SEQ ID NOS: 4

<210> SEQ ID NO 1
<211> LENGTH: 747

```
<212> TYPE: DNA
<213> ORGANISM: Artificial Sequence
<220> FEATURE:
<223> OTHER INFORMATION: FAB7 Heavy Chain Polynucleotide

<400> SEQUENCE: 1
atggaatgga tctggatatt tctcttcctc ctgtcagtaa ctacaggagt ccattctcag        60
gtacagctgc agcagtcagg tccaggactg gtgaagccct cgcagaccct ctcactcacc       120
tgtggcatct ccggggacag tgtctctagc aacagtgctg cttggaactg gctcaggcag       180
tccccatcga gaggccttga gtggctggga agaacatact acaggtccaa gtggtataat       240
gattatgcag tatctatgaa gagtcgaata accatcaacc cagacacatc caggaaccag       300
ttctccctgc agttgaattc tgtgactccc gaggacacgg ctgtgtatta ctgtgcaagg       360
gatggagaaa taagttacga ctactactac tacggtatgg acgtctgggg ccgcggcacc       420
ctggtcaccg tctcgagcgc ttctacaaag ggcccatcgg tcttccccct ggcaccctcc       480
tccaagagca cctctggggg cacagcggcc ctgggctgcc tggtcaagga ctacttcccc       540
gaaccggtga cggtgtcgtg gaactcaggc gccctgacca gcggcgtgca caccttcccg       600
gctgtcctac agtcctcagg actctactcc ctcagcagcg tggtgaccgt gccctccagc       660
agcttgggca cccagaccta catctgcaac gtgaatcaca agcccagcaa caccaaggtg       720
gacaagaaag ttgagcccaa atcttgt                                           747

<210> SEQ ID NO 2
<211> LENGTH: 249
<212> TYPE: PRT
<213> ORGANISM: Artificial Sequence
<220> FEATURE:
<223> OTHER INFORMATION: FAB7 Heavy Chain Amino Acid

<400> SEQUENCE: 2

Met Glu Trp Ile Trp Ile Phe Leu Phe Leu Leu Ser Val Thr Thr Gly
1               5                   10                  15

Val His Ser Gln Val Gln Leu Gln Gln Ser Gly Pro Gly Leu Val Lys
            20                  25                  30

Pro Ser Gln Thr Leu Ser Leu Thr Cys Gly Ile Ser Gly Asp Ser Val
        35                  40                  45

Ser Ser Asn Ser Ala Ala Trp Asn Trp Leu Arg Gln Ser Pro Ser Arg
    50                  55                  60

Gly Leu Glu Trp Leu Gly Arg Thr Tyr Tyr Arg Ser Lys Trp Tyr Asn
65                  70                  75                  80

Asp Tyr Ala Val Ser Met Lys Ser Arg Ile Thr Ile Asn Pro Asp Thr
                85                  90                  95

Ser Arg Asn Gln Phe Ser Leu Gln Leu Asn Ser Val Thr Pro Glu Asp
            100                 105                 110

Thr Ala Val Tyr Tyr Cys Ala Arg Asp Gly Glu Ile Ser Tyr Asp Tyr
        115                 120                 125

Tyr Tyr Tyr Gly Met Asp Val Trp Gly Arg Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190
```

Thr Ser Gly Val His Thr Phe Pro Ala Val Leu Gln Ser Ser Gly Leu
              195                 200                 205

Tyr Ser Leu Ser Ser Val Val Thr Val Pro Ser Ser Leu Gly Thr
            210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys
                245

<210> SEQ ID NO 3
<211> LENGTH: 705
<212> TYPE: DNA
<213> ORGANISM: Artificial Sequence
<220> FEATURE:
<223> OTHER INFORMATION: FAB7 Light Chain Polynucleotide Sequence

<400> SEQUENCE: 3

```
atggactggt ctcctctcct cctcactctc ctcgctcact gcacagggtc ctgggcccag      60
tctgtcctga cgcagccgcc ctcagcgtct gggacccccg ggcagagggt caccatctcc     120
tgttctggca gcagctccaa catcggaaat aatggtgtga actggtacca acaagtccca     180
ggaaagcctc ccaaactcct catctattat gatgatctgc tgccctcagg ggtctctgac     240
cgattctctg gctccaagtc tggcacctca gcctccctgg ccatcagtgg gctccagtct     300
gaggatgagg ctgattatta ctgtgaagcg tgggatgaca gtctggatgg tgtggttttc     360
ggcggaggca ccaagctgac cgtcctaggc cagcctaagg ctgcacccag tgtcactctg     420
ttcccgccct cctctgagga gcttcaagcc aacaaggcca cactggtgtg tctcataagt     480
gacttctacc cgggagccgt gacagtggcc tggaaggcag atagcagccc cgtcaaggcg     540
ggagtggaga ccaccacacc ctccaaacaa agcaacaaca gtacgcggc cagcagctac      600 ctgagcctga cgcctgagca gtggaagtcc cacagaagct acagctgcca ggtcacgcat     660
gaagggagca ccgtggagaa gacagtggcc cctacagaat gttca                    705
```

<210> SEQ ID NO 4
<211> LENGTH: 235
<212> TYPE: PRT
<213> ORGANISM: Artificial Sequence
<220> FEATURE:
<223> OTHER INFORMATION: FAB7 Light Chain Polynucleotide

<400> SEQUENCE: 4

Met Asp Trp Ser Pro Leu Leu Leu Thr Leu Leu Ala His Cys Thr Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Ser Asn Ile
            35                  40                  45

Gly Asn Asn Gly Val Asn Trp Tyr Gln Gln Val Pro Gly Lys Pro Pro
        50                  55                  60

Lys Leu Leu Ile Tyr Tyr Asp Asp Leu Leu Pro Ser Gly Val Ser Asp
65                  70                  75                  80

Arg Phe Ser Gly Ser Lys Ser Gly Thr Ser Ala Ser Leu Ala Ile Ser
                85                  90                  95

Gly Leu Gln Ser Glu Asp Glu Ala Asp Tyr Tyr Cys Glu Ala Trp Asp
            100                 105                 110

Asp Ser Leu Asp Gly Val Val Phe Gly Gly Gly Thr Lys Leu Thr Val
        115                 120                 125

```
Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235
```

METHOD FOR IDENTIFYING COMPOUNDS OF THERAPEUTIC INTEREST

CROSS REFERENCE TO RELATED APPLICATIONS

This application is a U.S. national phase of International Application No. PCT/EP2013/063747 filed on Jun. 28, 2013, which claims priority to U.S. Provisional Patent Application No. 61/849,830 filed on Jun. 28, 2012, the disclosures of each of which are explicitly incorporated by reference in their entirety herein.

The present invention relates to an improved method for identifying compounds of therapeutic interest employing antibody-protein target interactions to help present and/or hold the protein in a conformation that exposes or presents a binding site that has the potential to modify the protein function and which may be occluded in the "natural" conformation.

Thus in the present disclosure antibodies are employed as a tool to facilitate chemical drug discovery.

Whilst not wishing to be bound by theory the present inventors believe that proteins and fragments are subject to constant dynamic flux in vivo. This is certainly true for various complicated proteins such as ion channels which have active states, resting states, closed states and the like. However, it is theorised by the present inventors that these fluxes are more fundamental and not simply limited to complicated proteins like ion-channels. In support of the present disclosure this has been illustrated employing kinetic modelling and stopped-flow kinetic analysis on human IgE, which is discussed below.

As antibodies have exquisite specificity and potentially high binding affinity in essence they can bind proteins and elicit conformational changes, for example driving the equilibrium in a given direction.

These conformational changes often have function-modifying effects on the proteins, for example the protein may no longer be able to bind its natural ligand or the protein may no longer be able to initiate cell signalling or similar.

Thus some of the function-modifying characteristics of certain antibodies are due to their ability to hold the protein in a particular conformation.

Whilst a number of antibodies have been developed as therapeutics and a number are in the development pipeline there is no doubt that antibodies are less than suitable for use in the treatment of a number of diseases, for example one of the main disadvantages of antibodies is that to date they cannot be administered orally. A further disadvantage is that they are relatively expensive to develop and manufacture. These disadvantages may limit the use of antibody therapeutics to the most serious disease categories.

Horn and Shoichet (Allosteric inhibition through core disruption. J. Mol. Biol. 336, 1283-1291 (2004)) observed two inhibitors of β-lactamase that bound to an allosteric site, which had been created by engagement of the inhibitors themselves, between two helices of β-lactamase. Distortion of the catalytic residue, Arg244, was achieved through transmission of conformational changes, even though the small-molecule binding site was 16 Å away. This study also illustrates the magnitude of the task in the theoretical prediction of allosteric sites for small molecules from apo structures of proteins, because it would be very challenging to predict such a specific gross movement of the protein using computer simulation.

Classic small molecule discovery has been limited, to date, to identifying compounds based on screening with the recombinant "native" protein and the surface properties and characteristics thereof. Generally the native protein or fragment is fixed to a plate and used to screen libraries.

The present disclosure is based, in part, on the realisation that this traditional approach significantly limits the opportunities for finding compounds which modify functionally a relevant biological activity of the protein in question, and what is more it would be useful to freeze-frame the protein in a conformation or perspective for the purposes of screening.

Therefore, for a number of reasons it would be useful to have a C-change in the way that synthetic chemical modulators of biological activity are identified to gain access to hitherto untapped areas of chemical modulators.

The present inventors believe that function-modifying antibodies can be used to hold a protein or fragment thereof in a conformation that is different to that presented by the unbound protein, thereby exposing previously occluded areas and allowing identification of chemical modifiers directed thereto.

There are however, some practical difficulties associated with a screening approach using a library of compounds, namely the number of chemical compounds is potentially huge somewhere in the region of $10^{60}$ compounds. Therefore it is not possible to screen all these compounds and instead chemical diversity can be represented by a library of compounds comprising low molecular weight chemical fragments of 350 Da or less.

However, detecting binding events of these low molecular compounds especially in a non-competitive assay is challenging because in comparison to the large molecular weight of the target protein the change in molecular weight from a compound binding may be negligible.

Surprisingly the present inventors have established that the screening of the small changes in molecular weight from binding a compound fragment of 350 Da or less can be enabled by employing antibodies with a slow dissociation constants.

Thus in one aspect there is provided a method of identifying compounds capable of binding to a functional conformational state of a protein of interest or protein fragment thereof, said method comprising the steps of
  (a) Binding a function-modifying antibody to the target protein of interest or a fragment thereof to provide an antibody-constrained protein or fragment, wherein the antibody has binding kinetics with the protein or fragment which are such that it has a low dissociation rate constant,
  (b) Providing a test compound which has a low molecular weight,
  (c) Evaluating whether the test compound of step b) binds the antibody constrained protein or fragment, and
  (d) Select a compound from step c) based on the ability to bind to the protein or fragment thereof.

Target Protein

A target protein of the present invention can be any kind of protein or polypeptide amenable to influence by the binding of another molecule. Typical categories of targets include, but are not limited to enzymes, cytokines, receptors, transporters and channels. In certain embodiments the target protein is known to have a function in disease onset, development or establishment. In the present invention compounds are identified which modulate the activity of the target protein in a desirable way, for example modulation of the proteins biological activity, such as inhibition of the activity of the target protein or stimulation of the activity of the target protein.

Protein and polypeptide are employed herein interchangeably unless the context indicates otherwise.

The target polypeptide for use in the present invention may be the 'mature' polypeptide or a biologically active fragment or derivative thereof. Target polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The target polypeptide may in some instances be part of a larger protein such as a fusion protein, for example fused to an affinity tag. In some instances the target protein may be expressed naturally on the surface of a cell and cell surface expressed protein may be used, either as recombinant cells or naturally occurring cell populations.

It will be appreciated that the exact nature of the target protein used in the method of the present invention may vary at different stages of the method, for example fragments or domains or mutations of the target protein may be used in certain screens or structural representations, where appropriate.

In one example the target protein is human IgE.

In one example the target protein is not a G-protein coupled receptor (GPCR).

The antibody for use in the present invention holds the target protein in a functional conformational state, typically active or inactive. Typically this is a desired functional conformational state compared to the unbound target protein. For example the desired functional conformational state may be more or less active than the unbound target protein depending on the desired outcome.

In one embodiment a function-modified state (or functional conformational state) generated by binding of an antibody can be measured in a functional assay and can be identified by comparison to the performance of the corresponding native protein or fragment in the assay.

In the majority of embodiments it is envisaged that the antibody will hold the protein in a conformation that is inactive or has reduced activity in a relevant biological respect, for example prevents binding to a ligand or prevents initiation of a signalling cascade.

However if the method is employed in a high-through put scale a number of different antibodies may be employed in a matrix type experiment, for example wherein binding characteristics of different chemical entities to a given protein or fragment are studied in parallel, wherein the protein or fragment molecules are each constrained by the same or different antibodies holding the protein in different conformations.

In one embodiment an array of the same antibody holding a particular (the same) protein can be employed. This allows the protein or fragment to be incubated with a diverse range of compounds.

In one embodiment an array employing the same protein and different antibodies constraining it is employed in the method. Compounds screened in this embodiment may be prioritised based on a high frequency of binding to the protein when constrained in a number of antibody complexes. Essentially the more binding events that occur for a given compound the more important or interesting the compound could be.

In one embodiment the antibody employed in step a) is pre-screened to establish if the antibody possesses the ability to modify a functional activity of the target protein or fragment.

Function-modifying antibody as employed herein refers to the ability of the antibody in vitro and/or in vivo to agonise, antagonise, block, neutralise or inhibit a therapeutically relevant activity of the target protein, for example prevent binding to a natural ligand and/or prevent initiation of a signalling cascade.

In one example the antibody may be a 'neutralising antibody', i.e. an antibody that is capable of neutralising the biological activity of a given protein, such as signalling activity, for example by blocking binding of a target protein to one or more of its receptors.

In one embodiment one or more antibodies employed in the methods of the present disclosure are allosteric inhibitors of a relevant biological activity in the protein or fragment.

In one embodiment there is provided a compound or fragment identified by the method which modifies a biological activity of a target protein, for example which inhibits a biological activity of a target protein.

In one embodiment the compound identified is an allosteric modulator, such as an allosteric inhibitor.

Allosteric modulator refers to where a biological function of the target protein or fragment is modulated by binding that is not, for example, in the natural binding site of the natural ligand for the protein or fragment.

Allosteric inhibitor as employed herein refers to non-competitive inhibition that may, for example be effected by a change of the shape of the active site caused by binding of the inhibitor at a site removed from the active site, and includes an allosteric antibody.

Allosteric modulation offers a particularly promising mechanism whereby small molecules, for example may modulate protein—protein interactions. It has been suggested that all dynamic proteins have a potential for allosterism, which leads to altered conformational redistribution of the protein surface. The placement of a compound in a site protected from direct competition (with a relatively high affinity interaction) and also from solvent may bring about the required biological effect through conducted distortion and subsequent rearrangement or perturbation of a specific interface.

Suitable screens for determining the activity of each target protein may be known in the art or can be devised experimentally, employing known techniques. Such screens therefore allow the effect of an antibody employed in the method or candidate compound on the activity of the target protein to be determined. Such screens include, for example signalling assays, detecting receptor/ligand interactions or enzyme activity assays. It will be appreciated that each screen will depend on the nature of the target protein and that more than one screen may be used.

In the method of the present invention, candidate compounds, compound fragments or antibodies may each be tested for their effect on the biological activity of the target protein. For example, the antibodies and compounds identified which bind to the target protein may be introduced via standard screening formats into biological assays to determine the inhibitory or stimulatory activity of the compounds or antibodies, or alternatively or in addition, binding assays to determine binding or blocking, such as ELISA or BIAcore may be appropriate, alternatively or additionally the ability of the antibody or the compound to induce structural alterations may be identified using for example FRET based assays as described herein.

The small molecule compound identified by the method of the present invention may similarly block binding of the target protein to one or more of its receptors and neutralise the biological activity of the protein.

As used herein with reference to the activity of the target protein the terms 'modulate' and 'alter' are used interchangeably.

The concept of the present invention has been illustrated herein by reference to human immunoglobulin E (IgE) (Uniprot P01854). IgE consists of a dimer of two identical heavy and two identical light chains, but unlike IgG in which the antigen-binding Fab region is separated from the receptor-binding Fc region by a flexible hinge, IgE contains an additional disulphide-linked pair of domains, (Cε2)2, in the place of IgG's hinge1. FRET assays and X-ray and neutron scattering studies in solution have indicated that IgE and IgE-Fc adopts an asymmetrically bent conformation that was subsequently observed in the crystal structure of IgE-Fc (FIG. 2a)[6]. In this bent structure, the (Cε2)2 domain pair folds back onto the Cε3-Cε4 domains, forming an extensive intra-molecular interface (of about 1520 Å$^2$). The structure of the complex of IgE-Fc bound to the extracellular domains of the FcεRI α-chain also showed that the bend becomes even more acute upon receptor binding'.

Although the Cε2 domains are not directly involved in binding FcεRIα, they do contribute to the kinetics of the interaction, decreasing both the association and dissociation rate constants[7,8].

The present disclosure provides an open flatter IgE structure, which is inactive. This is discussed in more detail in the Examples herein below.

Antibodies

Function modifying antibodies for use in the present invention may be obtained using any suitable method known in the art. Preferably the function-modifying antibodies obtained prior to step (a) of the method are generated using one or more of the methods described herein below and using a target protein as described herein above. In one example the function-modifying antibodies of the present invention are not generated by using the target protein in co-complex with a small molecule compound, such as an inhibitor, antagonist or agonist of the target protein.

The target polypeptide or cells expressing the target polypeptide can be used to produce antibodies which specifically recognise the target polypeptide. Antibodies generated against the target polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, pigs or camelids (e.g. camels, llamas) may be immunized.

In one example the antibody of the present invention binds human IgE.

In one example the present invention provides an antibody which binds human IgE comprising the sequences provided in FIG. 14, in particular the sequences provided in SEQ ID NOs 2 and 4, lacking the signal sequences. In particular the heavy chain variable region sequence (without the signal sequence) comprising residues 20-144 of SEQ ID NO:2 and the light chain variable region sequence (without the signal sequence) comprising residues 20-129 of SEQ ID NO:4. Also provided is the heavy chain sequence comprising residues 20-249 of SEQ ID NO:4 and a light chain comprising residues 20-235 of SEQ ID NO:4.

Antibodies for use in the present invention include whole antibodies of any suitable class for example, IgA, IgD, IgE, IgG or IgM or subclass such as IgG1, IgG2, IgG3 or IgG4. and functionally active fragments or derivatives thereof and may be, but are not limited to, monoclonal, humanised, fully human or chimeric antibodies.

Antibodies for use in the present invention may therefore comprise a complete antibody molecule having full length heavy and light chains or an antigen binding fragment thereof and may be, but are not limited to Fab, modified Fab, Fab', F(ab')$_2$, Fv, single domain antibodies (such as VH, VL, VHH, IgNAR V domains), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9): 1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab[1] fragments described in International patent applications WO2005/003169, WO2005/003170 and WO2005/003171. Multi-valent antibodies may comprise multiple specificities e.g. bispecific or may be monospecific (see for example WO92/22853 and WO05/113605).

The term 'antibody' as used herein may also include binding agents which comprise one or more CDRs incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g. CDRs, a variable region etc.) in a localised surface region. Such structures can be a naturally occurring polypeptide or polypeptide 'fold' (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendramisat domains may be used (See for example, Nygren and Uhlen, 1997, Current Opinion in Structural Biology, 7, 463-469).

The term 'antibody' as used herein may also include binding agents based on biological scaffolds including Adnectins, Affibodies, Darpins, Phylomers, Avimers, Aptamers, Anticalins, Tetranectins, Microbodies, Affilins and Kunitz domains.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO92/02551; WO2004/051268 and International Patent Application number WO2004/106377.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

Chimeric antibodies are those antibodies encoded by immunoglobulin genes that have been genetically engineered so that the light and heavy chain genes are composed of immunoglobulin gene segments belonging to different species.

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced, for example by the phage display methods described above and antibodies produced by mice in which the murine immunoglobulin variable and constant region genes have been replaced by their human counterparts eg. as described in general terms in EP0546073, U.S. Pat. Nos. 5,545,806, 5,569,825, 5,625,126, 5,633,425, 5,661,016, 5,770,429, EP 0438474 and EP0463151.

In one example the antibodies for use in the present invention may be derived from a camelid, such as a camel or llama. Camelids possess a functional class of antibodies devoid of light chains, referred to as heavy chain antibodies (Hamers et al., 1993, Nature, 363, 446-448; Muyldermans, et al., 2001, Trends. Biochem. Sci. 26, 230-235). The antigen-binding site of these heavy-chain antibodies is limited to only three hypervariable loops (H1-H3) provided by the N-terminal variable domain (VHH). The first crystal structures of VHHs revealed that the H1 and H2 loops are not restricted to the known canonical structure classes defined for conventional antibodies (Decanniere, et al., 2000, J. Mol. Biol, 300, 83-91). The H3 loops of VHHs are on average longer than those of conventional antibodies (Nguyen et al., 2001, Adv. Immunol., 79, 261-296). A large fraction of dromedary heavy chain antibodies have a preference for binding into active sites of enzymes against which they are raised (Lauwereys et al., 1998, EMBO J, 17, 3512-3520). In one case, the H3 loop was shown to protrude from the remaining paratope and insert in the active site of the hen egg white lysozyme (Desmyter et al., 1996, Nat. Struct. Biol. 3, 803-811). Accordingly, whilst clefts on protein surfaces are often avoided by conventional antibodies, heavy-chain antibodies of camelids have been demonstrated to be capable of entering enzyme active sites, largely due to the compact prolate shape of VHH formed by the H3 loop (De Genst et al., 2006, PNAS, 103, 12, 4586-4591 and WO97049805).

It has been suggested that these loops can be displayed in other scaffolds and CDR libraries produced in those scaffolds (See for example WO03050531 and WO97049805). Accordingly as detailed herein above, scaffolds containing such loops and CDRs may be used in the present invention.

In one example the antibodies for use in the present invention may be derived from a cartilaginous fish, such as a shark. Cartilaginous fish (sharks, skates, rays and chimeras) possess an atypical immunoglobulin isotype known as IgNAR. IgNAR is an H-chain homodimer that does not associate with a light chain. Each H chain has one variable and five constant domains. IgNAR V domains (or V-NAR domains) carry a number of non canonical cysteines that enable classification into two closely related subtypes, I and II. Type II variable regions have an additional cysteine in CDRs 1 and 3 which have been proposed to form a domain-constraining disulphide bond, akin to those observed in camelid VHH domains. The CDR3 would then adopt a more extended conformation and protrude from the antibody framework akin to the camelid VHH. Indeed, like the VHH domains described above, certain IgNAR CDR3 residues have also been demonstrated to be capable of binding in the hen egg white lysozyme active site (Stanfield et al., 2004, Science, 305, 1770-1773.

Examples of methods of producing VHH and IgNAR V domains are described in for example, Lauwereys et al, 1998, EMBO J. 1998, 17(13), 3512-20; Liu et al., 2007, BMC Biotechnol., 7, 78; Saerens et al., 2004, J. Biol. Chem., 279 (5), 51965-72.

Given the ability of certain VHH, IgNAR and other such antibody domains and structures with protruding CDRs to bind into clefts on target proteins, in one example these antibodies are the preferred antibodies for use in the present invention. Also, given the convex nature of these CDRs the binding site on the target protein is often relatively small and focused, making these useful antibodies for identifying a cluster of closely situated contact atoms suitable for use in compound fragment growth. Accordingly in one embodiment an antibody for use in the present invention is a VHH antibody or epitope binding fragment thereof, such as a VHH domain antibody or one or more CDRs derived therefrom. In one embodiment an antibody for use in the present invention is an IgNAR antibody or epitope binding fragment thereof, such as a IgNAR V domain or V-NAR domain or one or more CDRs derived therefrom. In one embodiment an antibody for use in the present invention is a CDR3 containing antibody or scaffold protein comprising a CDR3 derived from a VHH domain antibody or an IgNAR antibody. Typically such antibodies or scaffolds contain CDR3 regions which are greater than 10 amino acids in length. In one example the CDR3 regions are greater than 20 amino acids in length. In one example the CDR3 regions are up to 30 amino acids in length. In one example the CDR3 regions are between 20 and 30 amino acids in length.

It is important that the antibodies employed in the method of the present disclosure have a slow dissociation rate constant ($k_d$ ($s^{-1}$)), this is more important than affinity alone. The slow dissociation rate constant ensures that the small weight changes from binding of a small molecular weight chemical entity of about 350 Da or less to the antibody-target protein complex may be more readily detected.

Generally a dissociation rate constant in the order of $1-9 \times 10^{-4}$ $s^{-1}$ or less is required, for example $1-9 \times 10^{-5}$ $s^{-1}$, 1-9×10⁻⁶ s⁻¹ or 1-9×10⁷ s⁻¹. For example 2×10⁻⁴ s⁻¹ or less, or 1×10⁻⁴ s⁻¹ or less is required, for example 1×10⁻⁵ s⁻¹, 1×10⁻⁶ s⁻¹ or 1×10⁷ s⁻¹.

Dissociation rate constants can be measured using techniques such as surface plasmon resonance e.g. BIAcore analysis which are routine in the art. For example, using surface plasmon resonance analysis the association rate constant ($k_a$) and the dissociation rate constant (kd) are obtained individually, and the dissociation constant (KD) value can be determined by the quotient of the rate constants ($k_d/k_a$).

In one example, for dissociation of a complex, where re-binding is not considered, the rate can be defined as:

$$dR/dt = -k_d R$$

Separating the variables and integrating gives:

$$R_t = R_0 \cdot e^{-kd(t-t_0)}$$

$$\ln(R_0/R_t) = k_d(t-t_0)$$

thus $k_d = \ln(R_0/R_t)/(t-t_0)$ where Rt represents the response at time t, and R0 is the response at time zero and t in seconds gives units of s−1

Antibodies with low association rate constants may be useful in the methods of the present disclosure because they may allow access to rare conformational states.

Where the antibody has a low association rate constant this will need to be factored into the method design, for example pre-incubation of the protein and the antibody may be required for a sufficient period to allow association.

Where phage display is used to generate the antibody or antibodies employed in the method herein, affinity maturation will generally be required to provide the appropriate properties, which is discussed in more detail below.

It will be appreciated that the dissociation rate constant of antibodies generated in the method of the present invention may be altered using any suitable method known in the art. Variants can be obtained by a number of maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In the present invention one or more antibodies are obtained which bind to the target protein and alter the activity of the target protein in a desirable way as determined using suitable screens, as described herein. In one embodiment one antibody or fragment thereof is generated for use in the method of the present invention. In one embodiment two antibodies or fragments thereof which bind the target protein are produced for use in the method. In one embodiment three antibodies or fragments thereof which bind the target protein are produced for use in the method. In one embodiment a panel of three or more antibodies or fragments thereof which bind the target protein and alter the biological activity of the target protein are produced for use in the method. It will be appreciated that such a panel of antibodies may comprise 3, 4, 5, 6, 7, 8, 9 or 10 or more antibodies. It will also be appreciated that each of the antibodies may modulate the activity of the target protein to the same or a different extent and that they may bind in the same, similar, overlapping or different locations on the target protein. Furthermore, each of the antibodies may be generated by the same or different means e.g. they may be obtained from the same or different species and/or may be the same or different types of antibodies, e.g. humanised or chimeric and/or they may be of different formats e.g. VHH or IgNAR domains. In another example more than one antibody may be derived from a single parent antibody, for example by mutagenesis, thus generating a panel of 2 or more related antibodies which bind the target protein at different locations and/or with different affinities and/or with varying abilities to modulate the activity of the target protein. Furthermore such mutagenesis may be used to generate panels of antibodies, through methods such as alanine scanning in order to help validate contact atoms on the antibody and/or to prioritise pharmacophore sites by allowing critical residues/contact atoms on both the antibody and the target protein to be identified. Accordingly, in one embodiment at least one of the antibodies employed in step (a) of the method is generated by mutagenesis of another antibody.

In one embodiment one antibody is employed to bind the target protein or fragment.

In another embodiment two antibodies are employed to bind a single protein or fragment.

In one embodiment an array of antibodies or binding fragments or a combination of the same for use in the present method are provided an a solid phase, such as a plate suitable for high-through-put screening or a sensor chip for use in SPR analysis.

In one embodiment an antibody is affixed to a plastic or resin bead.

In one embodiment an antibody-target protein complex may be affixed to a plastic or resin bead.

The antibodies employed in the array may be the same (monoclonal) or different (polyclonal).

In one embodiment the array employs a variety of monoclonal antibodies.

Methods for fixing antibodies to a solid phase, such as a plastic plate or sensor chip are well known in the art. The antibody may of course incorporate a tag, for example a his-tag, flag-tag or similar which can be used to indirectly fix the antibody to the plate or sensor chip via a reagent specific to the tag.

The antibody may be fixed to the solid phase, such as a plate before or after binding to the protein or fragment thereof.

In one embodiment the antibody binding to the target protein is effected in a liquid phase and optionally thereafter the complex or complexes formed are fixed to a solid phase such as a plate or sensor chip.

In one embodiment an antibody protein complex is formed in a liquid phase, and before it is employed in screening for compounds, it is subjected to a functional assay to establish if a relevant biological activity of the protein has been inhibited and/or the complex is subject to structural analysis to establish, for example where the antibody has bound. The latter can be established by, for example performing X-ray crystallography.

As discussed above in one embodiment a chemical fragment of 350 Da or less is employed in step b), for example a compound of about 300 Da such as 200, 210, 220, 230, 240, 250, 260, 270, 280 & 290 is employed. This is advantageous because it allows the relevant chemical diversity to be screened employing a more manageable library.

In one embodiment 1 to 10,000 compounds are screened, for example 100 to 9,000, 1,000 to 8,000; 2,000 to 7,000; 3,000 to 6,000 or 4,000 to 5,000 are screened. In one embodiment the screening for binding employs a non-competitive assay. This is advantageous because it allows the identification of chemical modifiers for sites where there are no known ligands. This significantly increases the opportunity for finding binding sites which modify biological activity.

In one embodiment 1 to 30,000 compounds are screened, for example 20,000 to 30,000 compounds are screened The evaluation of binding of the compound to the antibody-protein complex will generally be performed by surface plasmon resonance, such as BIAcore analysis.

After an initial analysis that establishes binding has taken place further structural analysis may be performed to generate three-dimensional structural information, for example X-Ray crystallography analysis, which is discussed in more detail below.

The structural information gained from the latter analysis may be used in computational modelling or analysis to predict or suggest chemical modifications that may be desirable to make the initial compound hit.

Of course this may be an iterative process where chemical modifications are made to the initial compound and the resulting compound is re-screened wherein the method may optionally include generating further three-dimensional information on the resultant compound. Typically re-screening, particularly in the early stages will take place using the antibody-target protein complex.

Once the potency of the chemical compound has reached an appropriate level and the binding is sufficient to locate and bind to the target protein in the absence of the antibody.

Antibody: Target 3D Structural Representation

In the present invention one or more antibodies are employed which bind to the target protein and alter the biological activity of the target protein in a desirable way (e g inhibit or stimulate activity) as determined using suitable screens as described herein.

In the present context more than one antibody may refer to two antibodies binding the same protein molecule or alternatively may refer to two antibodies binding different protein molecules of the same type. Each of these embodiments may be used in an array or matrix-type experiment.

In one embodiment a three dimensional structural representation of at least one such antibody in complex with the target protein is subsequently generated in order to obtain information about where the antibody is binding the target protein, the functional conformational state of the target protein and which amino acid residues and hence atoms on the target protein and the antibody are in contact with each other or interact with each other. This may be done prior to step a) or step b) if desired.

However, screening and/or structural analysis may also or alternatively be performed in the presence of a test compound.

Preferably, where more than one antibody has been employed which binds the target protein and modulates its activity, structural information is obtained for each of the antibodies in complex with the target protein. The functional conformational state revealed by the structural analysis may be previously known or unknown. In one example the functional conformational state revealed by the antibody-target protein structural analysis is new. In one example the structural analysis of the antibody-target protein reveals previously occluded structural features that are not available in the unconstrained protein. In one example these previously occluded structural features may be suitable targets for small molecule binding.

Any suitable method known in the art can be used to generate the three dimensional structural representation of an antibody:target protein complex. Examples of such methods include NMR and X-ray crystallography. Preferably X-ray crystallography is used. As set out herein above, the target protein may be the mature protein or a suitable fragment or derivative thereof.

Crystals will typically comprise crystallized polypeptide complexes corresponding to wild-type or mutated target protein in complex with an antibody or antibody fragment wherein the antibody fragment is for example an antibody VHH domain, IgNAR domain, dAb, Fab or Fab' fragment as described herein above. Such crystals include native crystals, in which the crystallized protein:antibody fragment complex is substantially pure and poly-crystals, in which the crystallised protein:antibody fragment complex is in association with one or more additional compounds, including but not limited to, inhibitors, antagonists, antibodies, or one or more receptor(s).

Preferably the crystals produced are of sufficient quality to permit the determination of the three dimensional X-ray diffraction structure of the crystalline polypeptide(s) to high resolution, preferably to a resolution of greater than about 3 Å, typically in the range of about 1 Å to about 3 Å. Generally crystals are grown by dissolving substantially pure polypeptide complexes in an aqueous buffer that includes a precipitant at a concentration just below that necessary to precipitate the polypeptide complexes. Water is then removed by controlled evaporation to produce precipitating conditions which are maintained until crystal growth ceases. Poly-crystals are prepared by soaking a native crystal prepared according to the above method in a liquor comprising the compound to be added to the poly-crystal of the desired complex. Alternatively, the poly-crystals may be prepared by co-crystallising the polypeptide complexes in the presence of the compound according to the method discussed above.

The three dimensional structural information obtained will typically include the atomic structure coordinates of the crystallised polypeptide complex or poly-complex, or the atomic structure coordinates of a portion thereof, such as, for example, information on a binding site or a neutralising epitope, but may include other structural information, such as vector representations of the atomic structures coordinates etc.

Preferably the three-dimensional structural information regarding the antibody-target protein complex comprises the atomic structure co-ordinates. Preferably the structural information comprises all or part of a binding site where the test compound has bound, if this is included.

Typically a test compound binding site of the present invention comprises one or more of the residues or atoms on the target protein that are in contact with or interact with said compound identified in the method of the present invention and one or more atoms on the compound that make those contacts or interactions with the target protein.

In one example the contact atoms on the target protein which fall within a binding site with the test compound are those that are in contact with or interact with any part of the compound.

In one embodiment further structural information is generated on a modified test compound to establish the effect on activity of certain chemical modifications to the initial test compound, for example the effect on the binding with the target protein.

The present inventors have generated a novel IgG antibody that binds to IgE-Fc and inhibits its interaction with FcεRIα, the crystal structure of the complex was solved using a Fab fragment of the IgG and revealed a new inactive conformational state for IgE, described in the Examples herein. In one example the present invention therefore provides a method of identifying compounds capable of binding to a functional conformational state of a human IgE, said method comprising the steps of:

(a) Binding a function-modifying antibody to human IgE or a fragment thereof to provide an antibody-constrained IgE or fragment, wherein the antibody has binding kinetics with the human IgE or fragment which are such that it has a low dissociation rate constant, (b) Providing a test compound which has a low molecular weight, (c) Evaluating whether the test compound of step b) binds the antibody constrained protein or fragment, and (d) Select a compound from step c) based on the ability to bind to human IgE or fragment thereof.

Compound Fragment Screening

In the method of the present invention the ability of test compound fragments to bind the antibody constrained protein is determined. In one example the compound selected in step (d) of the method does not bind the unconstrained target protein. In one example the compound selected in step (d) of the method does not bind the antibody in the absence of target protein. In one example the compound selected in step (d) of the method does not bind the unconstrained target protein or the antibody alone. In one example of the method of the present invention step c) further comprises evaluating whether the test compound of step b) binds the protein or fragment in the absence of antibody and step (d) further comprises selecting a compound from step c) based on the ability of the test compound to only bind the antibody-constrained protein or fragment and not the unconstrained protein or fragment.

Typically in later screening stages following further elaboration of the compound fragments identified by the method and once the potency of the chemical compound has reached an appropriate level the target protein binding is sufficient to allow the compound to bind the target protein in the absence of the antibody.

Typically the method of screening a compound according to step b) and c) is performed in the presence of the antibody-protein complex and binding to the target protein is detected in step (c).

In one embodiment the method of screening a compound according to step b) and c) is performed in the presence of an antibody-protein complex where a first test compound is already bound. In one embodiment this allows the chemical complexity of the test compound one to be built up by establishing what pharmacophores are able to bind in the presence of test compound-one. If a second compound is identified which binds in the presence of compound-one in theory the structures of the two compounds could be linked and optionally modified or rationalised to provide a new compound with improved binding and/or activity.

In one embodiment screening for binding of a third compound is performed in the presence of compound one and/or two.

In one example at least one contact atom on the target protein in a test compound binding site is identified. In one example at least one contact atom in a test compound that binds within the binding site identified. In one example at least one contact atom on the target protein and the corresponding contact atom in the test compounds that interacts with it is identified i.e. at least one pair of atoms are identified. The intermolecular interactions between the test compound and target protein atom are typically electrostatic interactions, hydrogen bonds and van der Waals non-polar interactions.

Where more than one contact atom pair is identified in a given binding site e.g. one on the target protein and one in the test compound, the protein contact atoms are preferably within a suitable distance of one another to be useful in subsequent fragment growth, as described herein below. In one example the contact atoms identified in the binding site will ideally be within a suitable distance of one another, typically about 1 Å to about 30 Å based on the shortest non-covalent atomic interaction or hydrogen bond distance and the longest distance between protein atoms that can be considered within the same binding site. The identified protein contact atoms can be prioritised through experimental protein mutagenesis studies or computational methods such as molecular mechanics free energy calculations [Moreira et al. J Comput Chem. 2007 February; 28(3):644-54].

In step (c) of the method of the present invention one or more compound fragments that bind the target protein are identified.

Compound fragments for use in the present invention, for example screening compounds typically have a molecular weight of less than 350, 340, 320, 310, 300, 290, 280, 270, 260, 250 Da. In one example the compound fragments have a molecular weight of less than 250, 240, 230, 220 Da. In one example the compound fragments have a molecular weight of less than 200 Da. Such fragments are typically small, simple compounds, usually consisting of no more than one or two rings with a few substituents.

It is likely that subsequent to finding a chemical fragment that binds the protein of interest (a hit), further elaboration of the chemical fragment will be require to improve the affinity of the binding interaction.

By screening libraries of such compound fragments it is usually possible to identify small compound fragments that bind very efficiently to the target protein, albeit only through a low number of interactions with the target protein, hence these are usually low affinity interactions. These compound fragment hits can be considered building blocks that can be combined e.g. merged or linked, to form larger and potentially much more potent and drug-like lead compounds. Alternatively, these hits can be 'seeds' or 'anchor points' which can be synthetically expanded into lead compounds, picking up increasingly more interactions with the target protein. In one example a mixture of both approaches may be used to generate subsequent compounds for screening.

Typically fragment-based screening involves screening a number of compound fragments, typically several thousand compounds, to find low-affinity fragments with Kd values in the high micromolar to millimolar range. For a review of fragment based screening methods see Hajduk and Greer, 2007, Nat. Rev. Drug. Discov. 6(3), 211-219.

Suitable compound fragment libraries may be designed using any suitable methods known in the art, whereby selection of compound fragments for inclusion in the libraries may be based on the presence or absence of desirable or undesirable chemical functionality and other constraints may be placed on the library such as solubility, shape, flexibility or spectral properties. Additionally, the strategy for subsequent chemistry on the fragments can also influence the design of the library. A review of fragment library strategies is provided in Baurin et al., 2004, J. Chem. Inf. Comput. Sci, 44, 2157-2166; Hubbard et al., 2007, Curr. Opin. Drug Discov. Devel., 10, 289-297; Zartier and Shapiro, 2005, Curr. Opin. Chem. Biol., 9, 366-370.

In the method of the present invention compound fragments are screened for binding to the antibody constrained target protein, either directly or virtually. The binding information can be obtained using any suitable method known in the art. For example an overview of the different approaches is given in the book 'Fragment-based approaches in drug discovery' (Jahnke, Erlanson, Mannhold, Kubinyi & Folkers (2006), published by Wiley) and also the review of Rees and coworkers (Rees et al. (2004) Nature Rev. Drug Discov. 3, 660-672).

Experimental methods useful for determining binding of compound fragments to proteins include but are not limited to:

*Protein X-ray crystallography* [Hartshorn et al. (2005) J. Med. Chem. 48, 403-41 3]. Efficient fragment screening using protein X-ray crystallography requires the soaking of cocktails of fragments into pre-formed crystals of a target protein. After collection of the X-ray data, the identification of the fragments from the cocktail is reliant on manual or automated analysis of the resultant electron density. The outcome of these studies is information regarding which fragments bind to the protein target and the actual binding configuration in the active site. No information is obtained on the actual binding strength or affinity.

*NMR-based screening* [Shuker et al. (1996) Science 21A, 1531-1534], or Structure-Activity-Relationship (SAR) by NMR, involves identifying and interpretation of the chemical shifts in the NMR spectrum as a result of the fragment to a target protein of interest. The result is information regarding the fragments that bind to the protein target. Typically, no information is obtained of the actual binding strength or affinity. Target Immobilized NMR screening may also be used (Vanwetswinkel et al., 2005, Chemistry & Biology, 12(2): 207-216).

The use of disulfide bonds to stabilize the binding of a fragment to the target protein [DeLano (2002) Curr. Opin. Struct. Biol. 12, 14-20]. This is achieved by placing a sulfur-containing amino acid called a cysteine on the surface of the protein and to screen the protein against a collection of sulfur-containing fragments. Fragments that bind near the cysteine form disulfide bonds with the protein, increasing the weight of the protein and allow the detection of the fragments by mass spectrometry. The outcome is a list of fragments that bind to the protein. No particular information is obtained regarding the fragments binding strength.

Microcalorimetry-based fragment screening has been described in an application note of MicroCal LLC (USA) ['Divided we fall? Studying low affinity real molecular species of ligands by ITC', MicroCal LLC, USA, 2005] in which the heat generated by the fragment-protein binding process is measured and converted in thermodynamical parameters such as entropy and enthalpy measures. The outcomes of the experiments are the identities of the binding fragments and optionally the corresponding binding affinities.

In-vitro binding assays which have been adapted to measure the binding of low affinity fragments have also been described [Boehm et al. (2000) J. Med. Chem. 43, 2664-2674]. The results of these experiments are a set of fragments with their corresponding binding affinities for a particular protein target.

Sedimentation analysis is a novel technology that has been described to measure fragment/protein interactions [Lebowitz et al. (2002) Protein Sci. 11, 2067-2079]. Sedimentation equilibrium measures the concentrations of the components at equilibrium in solution, and the readout from an sedimentation equilibrium experiments is an absorbance versus distance curve. The outcomes of the experiments are the identities of the fragments that show binding affinity for a particular protein target.

Solid-phase detection is a general term covering a wide range of technologies that share a common working principle in which both a bioreceptor and a signal transducer are combined to detect the binding of fragments to proteins. One specific example of SPR is BIAcore™, which has been used for screening fragment libraries (Metz et al., 2003, Meth. Principles. Med. Chem, 19, 213-236 and Neumann et al., 2005, Lett. Drug. Des. Discovery, 2, 590-594). Alternative solid-phase detection methods include but are not limited to the rupture event scanning (REVS) and resonant acoustic profiling (RAP) technologies commercialized by Akubio Ltd (UK), reflectance interference (RIf), total internal reflection fluorescence (TIRF), and the microcantelever technology as commercialized by Concentris GmbH (Suisse).

Capillary electrophoresis has also been mentioned as a tool to measure fragment/protein interaction [Carbeck et al. (1998) Ace. Chem. Res. 31, 343-350].

It will be appreciated that one or more of the methods described above may be used. For example NMR may be used to determine fragment binding and this may be combined with BIAcore™ screening to determine affinities and 'rank' the fragment hits identified. In one example BIAcore™ is used to simultaneously determine binding to the target protein and affinity.

Complementary to the experimental approaches mentioned above to generate fragment-binding data, information gathered from literature sources may also be useful in generating knowledge about the affinity of certain fragments to specific target proteins.

Whatever approach is used to collect the fragment binding data, the result is a list of compound fragment structures which are known, or believed, to bind to the target protein. Quantitative affinity information in the form of dissociation or $IC_{50}$ values is useful, but not essential.

It will be appreciated that once suitable structural information regarding the target protein-antibody interaction has been generated, virtual screening methods may be used to identify fragments that are expected to bind to the target protein. Virtual screening methods useful for determining binding of compound fragments to proteins include but are not limited to: GLIDE [Friesner et al J Med Chem. 2004 Mar. 25; 47(7):1739-49] and GOLD [Jones et al. J Mol Biol. 1997 Apr. 4; 267(3):727-48].

In one example the structure of the target protein-antibody crystal may be probed with a variety of different chemical fragments to determine optimal sites for interactions between such candidate molecules and the target protein. Small molecule fragments that would bind tightly to those sites can then be designed, and optionally synthesised and tested for their ability to bind to the target protein.

In another example computational screening of small molecule databases is used to identify chemical fragments that can bind in whole, or in part to the target protein. This screening method and its utility are well known in the art. For example, such computer modelling techniques have been described in WO97/16177 and WO2007/011392.

In one embodiment the computational screen further comprises the steps of synthesising the candidate fragment and screening the candidate fragment for the ability to bind the target protein as described herein above.

Typically one or more compound fragments which bind the target protein are identified in step (c) of the method of the present invention. In one example two or more fragments are identified. In one example three or more fragments are identified. In one example four or more fragments are identified. In one example five or more fragments are identified. In one example ten or more fragments are identified. In one example twenty or more fragments are identified. In one example fifty or more fragments are identified.

It will be appreciated that not all fragments identified may be selected for further 3D structural analysis, for example if a large number of fragments are identified. Certain fragments may be selected based on their synthetic tractability and/or likelihood of compliance with Lipinski's rule of five (Lipinski et al., 1997, Adv. Drug. Del. Rev, 23, 3-25).

Alternatively, or in addition, where the affinity of the fragments for the target protein has been determined this may be used to rank the fragments, such that those fragments with the highest affinity or ligand efficiency go on for further testing. Ligand efficiency is binding affinity normalised to the number of heavy atoms in the compound (i.e. potency/number of heavy atoms)

Alternatively or in addition, analogues of the compound fragments known to bind the target protein may be identified and selected based on for example, anticipated improved binding or synthetic tractability. It will be appreciated that these analogues could be tested for binding to the target protein either directly or virtually.

Alternatively or in addition compound fragments may be ranked based on competition assays conducted using one or more of the antibodies identified as described herein above, such that those fragments which bind in the same region as one or more of the antibodies identified are selected e.g. those compound fragments that cannot bind the target protein in the presence of the antibody are preferentially selected.

It may be that a combination of the different factors described above may be used to select one or more compound fragments for using 3D structural analysis.

3D Structural Analysis of Compound Fragments

In the method of the present invention a three dimensional structural representation may be generated for one or more of the selected compound fragments in combination with the antibody constrained target protein. Suitable methods for such structural representations include X-ray crystallography and NMR. Preferably X-ray crystallography is used.

The three-dimensional structural representation generated provides information about how and where the compound fragment is binding the target protein. The key interactions identified using molecular modelling programs such as Sybyl [www.tripos.com] may be used to generate a pharmacophore for structure based drug design.

One or more compound fragments that bind the target protein identified by the method of the present invention are selected for use in the synthesis of one or more candidate small molecule compounds, for example by compound fragment growth.

In one example a compound fragment will be selected if it makes an intermolecular interaction with one or more protein contact atoms on the target protein. An intermolecular interaction would include an electrostatic interactions, hydrogen bonds or lipophillic van der Waals interactions.

It will be appreciated that steps of the method may be iterative and that the 3D structure a compound fragment in association with the target protein may be generated before another compound fragment is obtained. In addition steps (b), (c) and (d) may be repeated until a compound fragment that binds with the desired biological profile is identified.

Compound Fragment Growth

The goal of such target guided synthesis is to build up molecules in a modular way to produce assembled molecules which have a higher binding affinity for the target protein than their individual parts or fragments and which are able to exert a desired biological effect on the target protein.

Using the structural information obtained from the compound fragment(s)-target protein interaction and optionally the antibody-target protein interaction any suitable fragment assembly/growth/rational method may be used to grow the fragment(s) selected to generate novel small molecule candidate compounds. Such methods include but are not limited to SAR by NMR, dynamic libraries, analoguing and virtual screening.

Methods of fragment based lead generation and subsequent rational design of more potent hit analogues and small molecules are known in the art, see for example Szczepankiewicz et al., Journal of the American Chemical Society (2003), 125(14), 4087-4096; Raimundo et al., Journal of Medicinal Chemistry (2004), 47(12), 3111-3130, Braisted et al., Journal of the American Chemical Society (2003), 125(13), 3714-3715, Huth et al., Chemical Biology & Drug Design (2007), 70(1), 1-12, Petros et al., Journal of Medicinal Chemistry (2006), 49(2), 656-663, Geschwindner et al., Journal of Medicinal Chemistry (2007), 50(24), 5903-5911, Edwards et al., Journal of Medicinal Chemistry (2007), 50(24), 5912-5925 and Hubbard, et al., Current Topics in Medicinal Chemistry (2007), 7(16), 1568-1581.

Typically such methods of compound fragment growth include iterative structure-based drug design to optimise a lead compound. Methods also include 'analoguing' of the compound fragments to identify nearest neighbours or similar compound fragments to those identified by screening and these may then be screened for binding to the target protein.

Growing the fragment(s) identified can be performed by adding functionality that binds to additional sub-sites on the protein surface. This can be achieved by searching a database of available chemicals for compounds containing the same sub-structures as the fragment or by synthesizing small libraries that add functionality to key attachment points on the fragment. The position and orientation of binding of the fragment to the target protein and the structural information obtained from the antibody which binds in the same vicinity can be used to guide the computational search or library synthesis. It will be appreciated that where additional relevant structural information is available, such as ligand binding, this may also be used to guide fragment growth.

Accordingly, 'growing' the compound fragment may encompass a number of activities including adding functionality, making small libraries, searching databases, computational searching and/or 'analoguing'.

A series of new compounds may be generated and these may then be screened for improved affinity for the target protein and/or for improved binding to the target protein and/or improved potency and/or the ability to alter the biological activity of the target protein. It will be appreciated that this may involve iterative rounds of further chemistry and fragment growth, optionally incorporating one or more further interactions with contact atoms on the target protein identified from the antibody binding structural representations. Typically such further screening, particularly in the early stages of improving binding to the target protein will be done using target protein in complex with the antibody, as previously described herein above.

Accordingly in one embodiment the present invention provides a method of generating a candidate compound or library of candidate compounds that may be used to generate a small molecule compound that alters the activity of a target protein.

The candidate small molecule compound or compounds generated using these methods can then be tested for their ability to alter the biological activity of the target protein using suitable screening methods as described herein. Such small molecule compounds are typically <1200 Da in size, typically <1100, <1000, <900 or <650 Da in size and are not peptide mimics.

The one or more candidate compounds generated are tested for improved affinity for the target protein and/or improved potency and/or improved ligand efficiency and/or ability to alter the biological activity of the target protein. As set out above growth of the compound fragments may be iterative and any steps or combination of steps of the method may be repeated more than once.

A first test compound selected in step (d) will generally require further modification in order to generate a small molecule compound e.g. to improve the extent to which it modulates the activity of the target protein and/or to make the compound more drug-like. A compound selected in step (d) therefore may be a small molecule compound, as described herein below, which modulates the activity of the target protein to the required extent for use as a drug.

Alternatively a compound selected in step (d) may be a candidate compound requiring further chemistry and screening in order to generate a suitable small molecule compound.

Accordingly the method of the present invention further chemistry is optionally performed on a compound selected in step (d), optionally by repeating one of more steps of the method to grow the fragment selected in (d) to interact with one or more further contact atoms of the protein.

A final small molecule compound which is suitable for a candidate identified employing the present invention is typically less than 1200 Da in size, for example less than 650 Da in size and is not a peptide. In one example a small molecule compound of the present invention has a molecular weight of less than 600 Da. In one example a small molecule compound of the present invention has a molecular weight of less than 550 Da. In one example a small molecule compound of the present invention has a molecular weight of less than 500 Da.

In one example a small molecule produced by the method of the present invention complies with at least one, preferably all of Lipinski's rule of five (Lipinski et al., 1997, Adv. Drug. Del. Rev, 23, 3-25).

Accordingly in one example a small molecule produced by the method of the present invention contains no more than five hydrogen bond donors (nitrogen or oxygen atoms with one or more hydrogen atoms).

In one example a small molecule produced by the method of the present invention contains no more than ten hydrogen bond acceptors (nitrogen or oxygen atoms).

In one example a small molecule produced by the method of the present invention has an octanol-water partition coefficient log P of less than 5.

In one example a small molecule produced by the method of the present invention has no more than two violations of the following criteria:
contains no more than five hydrogen bond donors (nitrogen or oxygen atoms with one or more hydrogen atoms),
contains no more than ten hydrogen bond acceptors (nitrogen or oxygen atoms),
has an octanol-water partition coefficient log P of less than 5, and
A molecular weight of less than 500 daltons Compositions/Therapeutic Uses The compounds identified by the method of the present invention may be useful in the treatment and/or prophylaxis of a pathological condition, the present invention also provides a pharmaceutical or diagnostic composition comprising a compound of the present invention in combination with one or more of a pharmaceutically acceptable excipient, diluent or carrier. Accordingly, provided is the use of a compound of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides the compound produced by the method of the present invention for use in the treatment or prophylaxis of a pathological disorder that is mediated by the target protein or associated with an increased level of the target protein.

EXAMPLES

The present invention will now be described by way of example only, in which reference is made to:

FIG. 1 Shows a diagrammatic representation of the method according to the present disclosure.

Figure 2:
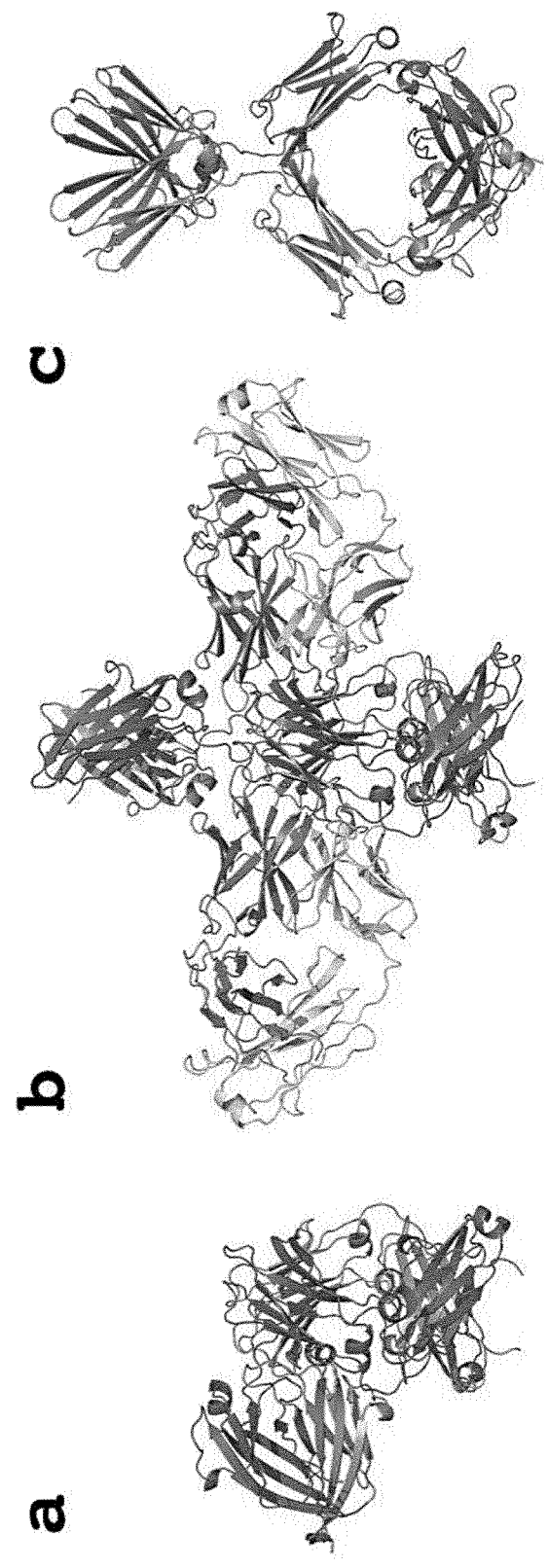

FIG. 2 Shows bent and extended structures adopted by IgE-Fc.
  a, the bent structure of free IgE-Fc, with the $(C\varepsilon 2)_2$ domain pair making contact with the $C\varepsilon 3$-4 domains,
  b, The structure of IgE-Fc bound symmetrically by two Fab molecules,
  c, The extended conformation of IgE-Fc as seen in the complex. The molecule has undergone an "unbending" of 120° compared to the free structure, resulting in a virtually two-fold symmetric structure.

FIG. 3 (A) Free-energy surface of the IgE-Fc unbending process generated through metadynamics simulation. Contours are drawn every 5 kJ/mol and coloured accordingly. The simulation covers the transition across the linear conformational states (at x=0) but does not encompass the complete "flip". The conformation seen in the $Fab^1$|IgE-Fc|$Fab^2$ complex is indicated (black cross). A possible pathway between energy minima is shown (dotted line). (B) Conformations of IgE-Fc corresponding to the energy minima in A are corresponding to the pathway indicated in A; numbers correspond to panels A and B.

FIG. 4 Shows ITC curves resulting from titration of IgE-Fc (a) or $Fc\varepsilon 3$-4 (b) into Fab, demonstrating that the Fab binding sites are accessible in both chains of both IgE-Fc and $Fc\varepsilon 3$-4. Titration of Fab into IgE-Fc (c) or $Fc\varepsilon 3$-4 (d), showing that the binding of $Fab^1$ and $Fab^2$ have different affinities.

Figure 5:
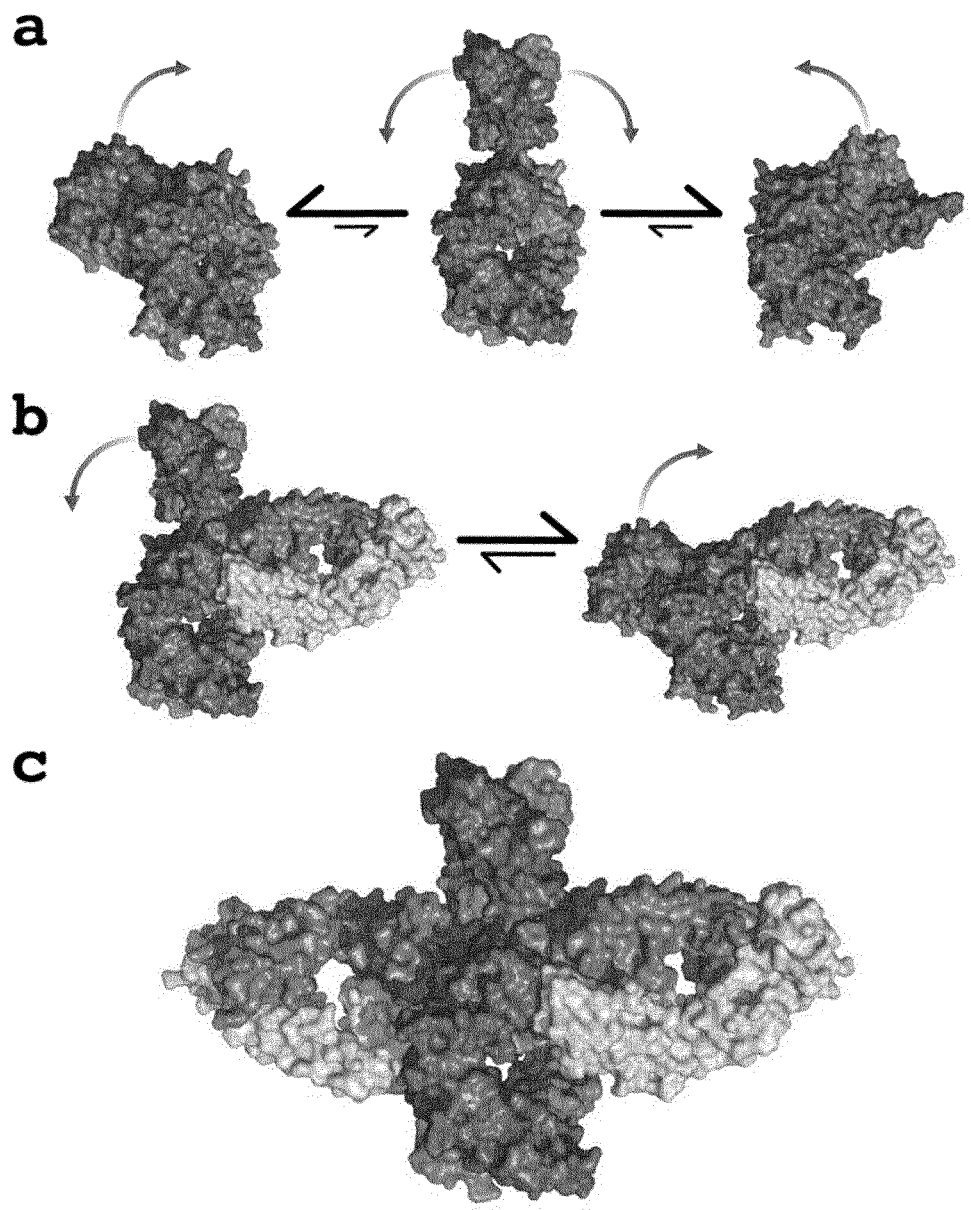

FIG. 5 Shows proposed mechanism of IgE-Fc flexibility and Fab binding in solution.
  a, IgE-Fc is predominantly bent in solution, but is capable of extreme flexibility whereby $(C\varepsilon 2)_2$ can flip from one side of the molecule to the other.
  b, $Fab^1$ engages either binding site of IgE-Fc, restricting the range of flexibility of the molecule. The bent conformation is energetically preferred and predominates. c, $Fab^2$ engages the extended form of IgE-Fc, capturing the molecule in this transiently occupied conformation.

Figure 6:
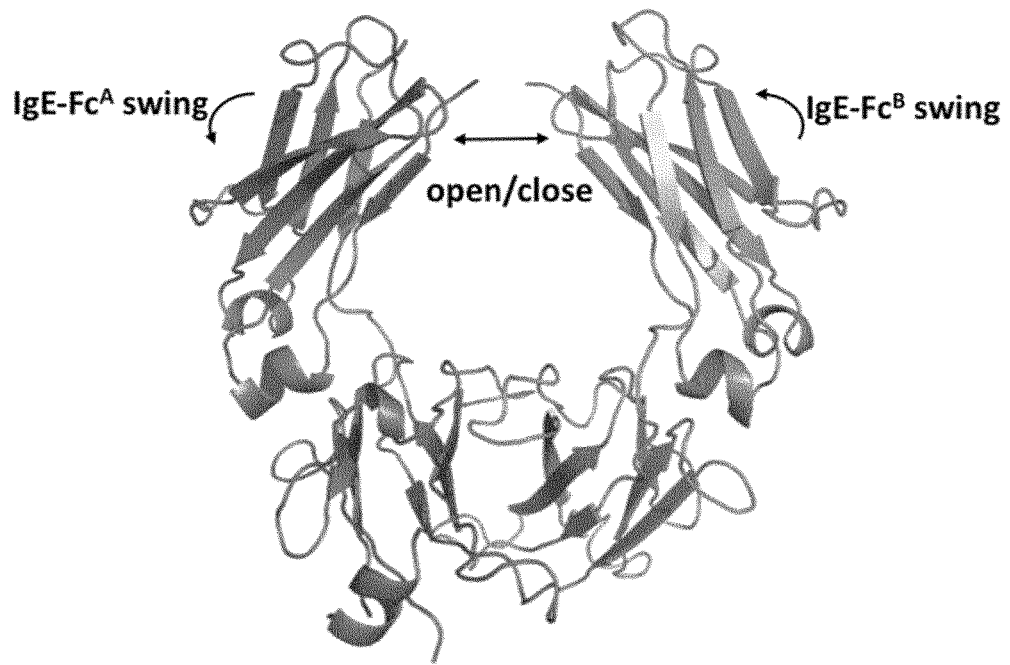

FIG. 6 Conformational flexibility of the Cε3 domains. Directions of "open/closed" and "swing" movements between the Cε3 domains are indicated on the free IgE-Fc structure (2WQR, Cε2 domains not shown for clarity). IgE-Fc$^A$ and IgE-Fc$^B$ are labelled.

Figure 7:
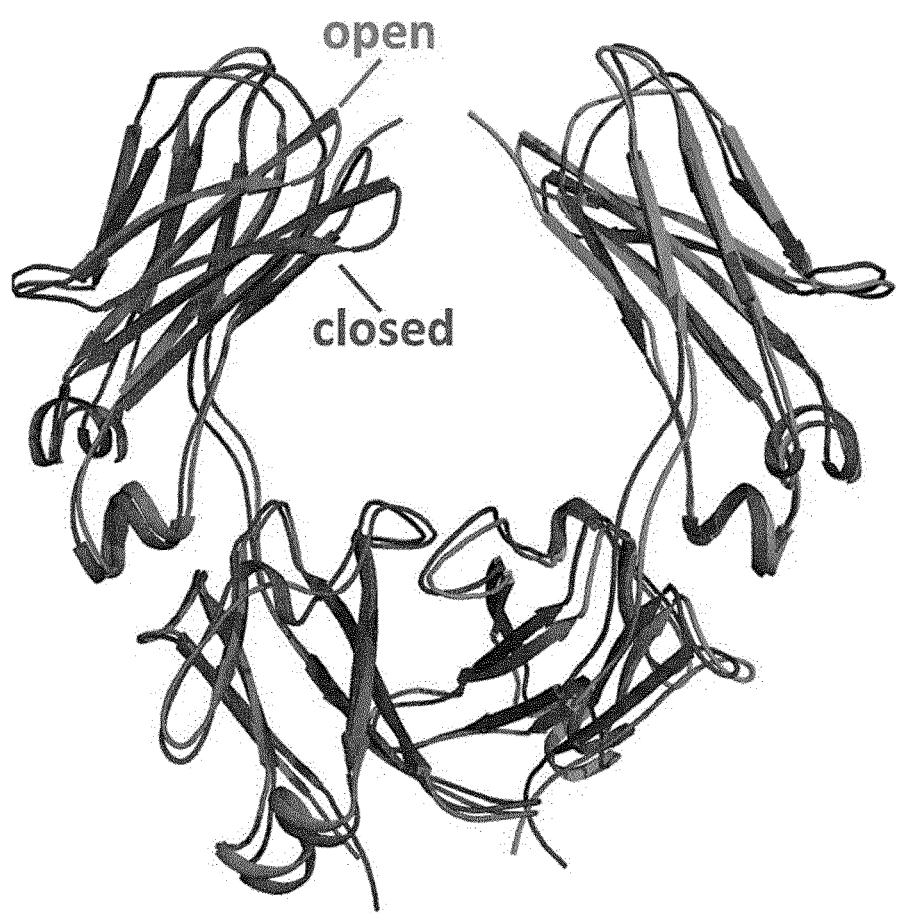

FIG. 7 Conformational change of the Cε3 domains of IgE-Fc on Fab binding. The Cε3 and Cε4 domains of the extended IgE-Fc structure as seen in the Fab complex (IgE-Fc$^A$ IgE-Fc$^B$) are overlayed on the Cε3 and Cε4 domains of free IgE-Fc (Cε2 domains not shown for clarity). In the structure of free IgE-Fc, IgE-Fc$^A$ is in the closed conformation, and IgE-Fc$^B$ is in the open conformation, while in the extended IgE-Fc structure, both chains are open. Open (extended IgE-Fc) and closed (free IgE-Fc) forms of IgE-Fc$^A$ are indicated.

Figure 8:
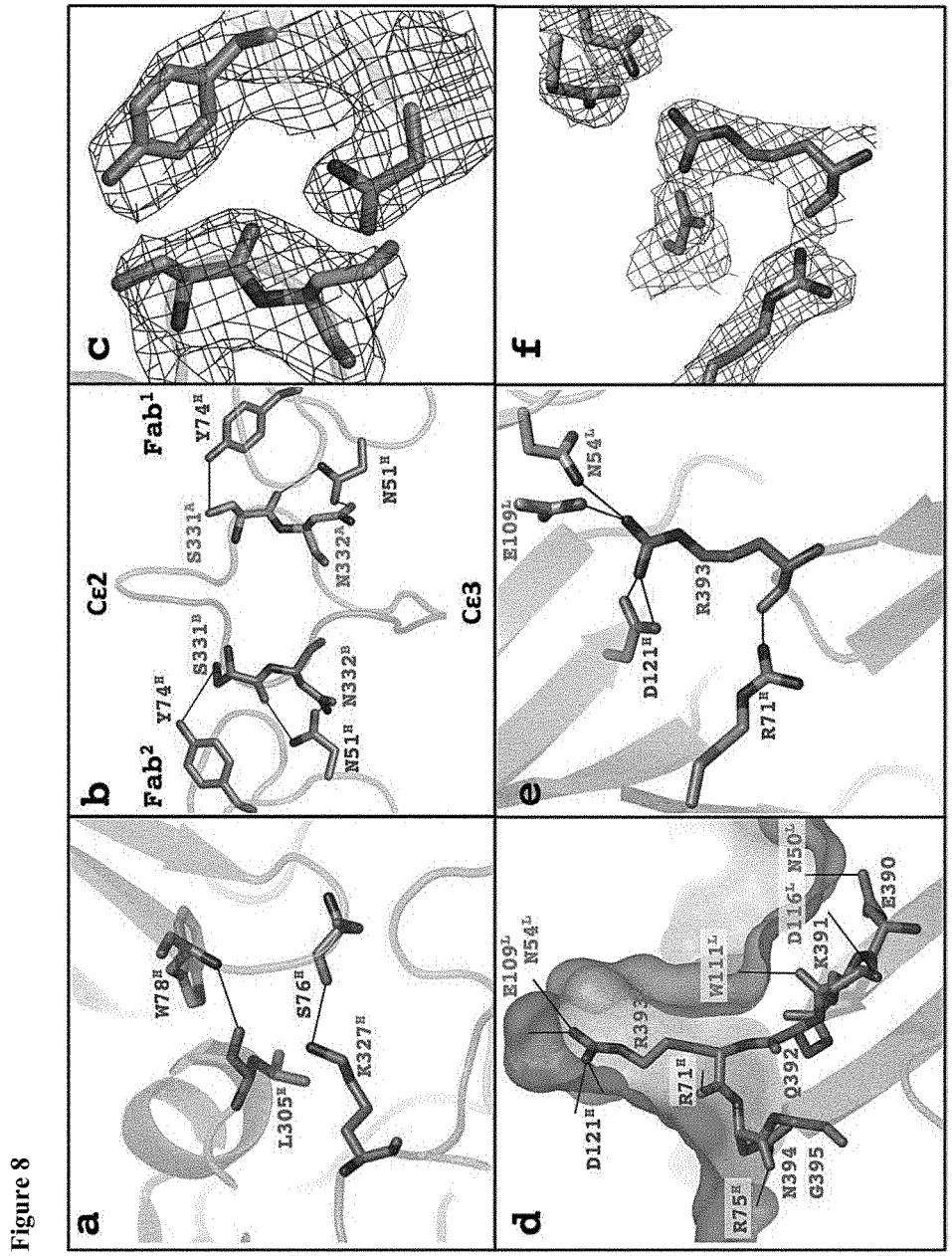

FIG. 8 Interactions between Fab and IgE-Fc. a, Interactions between Fab$^1$ heavy chain and the Cε2 domain of IgE-Fc$^A$. Hydrogen bonds are indicated by solid black lines. b, Contact between IgE-Fc Cε2-Cε3 linker regions and the Fab molecules. IgE-Fc$^A$ is shown in blue and IgE-Fc$^B$ in orange. The locations of the Cε2 and Cε3 domains are indicated. c, 2F$_o$-F$_c$ electron density at 1σ contour level for one set of interface residues shown in b. d, R393 binding pocket between Fab heavy (green) and light (grey) chains. Black lines indicate hydrogen bonds formed with Fab residues. e, 2F$_o$-F$_c$ electron density at 1σ contour level for the residues shown in d. e, The interactions between R393 and Fab residues.

FIG. 9 Structural basis for inhibition of IgE-Fc interaction with FcεRIα. a, The structure of IgE-Fc bound to FcεRIα shown in two orthogonal views. IgE-Fc is shown as a cartoon representation (IgE-Fc$^A$ in lighter shade, IgE-Fc$^B$ in darker shade), FcεRIα shown. b, Overlay of the Cε3 and Cε4 domains of IgE-Fc in receptor-bound and Fab-bound (IgE-Fc$^A$, IgE-Fc$^B$) conformations. The key residues involved in receptor binding are shown in space filling representation. An orthogonal view of just the Cε3 domains is also shown. c, Location of FcεRIα (space filling representation) after superposition of the IgE-Fc/FcεRIαcomplex onto the Fab$^1$|IgE-Fc complex (using the Cε4 domains). Steric interference of both (Cε2)$_2$ and Fab$^1$ with FcεRIα is observed.

FIG. 10 Stopped-flow kinetic binding curves showing the change in fluorescence when a, Fab binds to IgE-Fc and b, Fab binds to Fcε3-4. The top traces indicate experiments carried out with IgE-Fc in excess over Fab, and the bottom traces are experiments with Fab in excess over IgE-Fc or Fcε3-4.

FIG. 11 Concentration dependence of the stopped-flow binding kinetics, showing linearity for Fab binding to a, IgE-Fc and b, Fcε3-4.

FIG. 12 FRET analysis of antibodies

Figure 13:
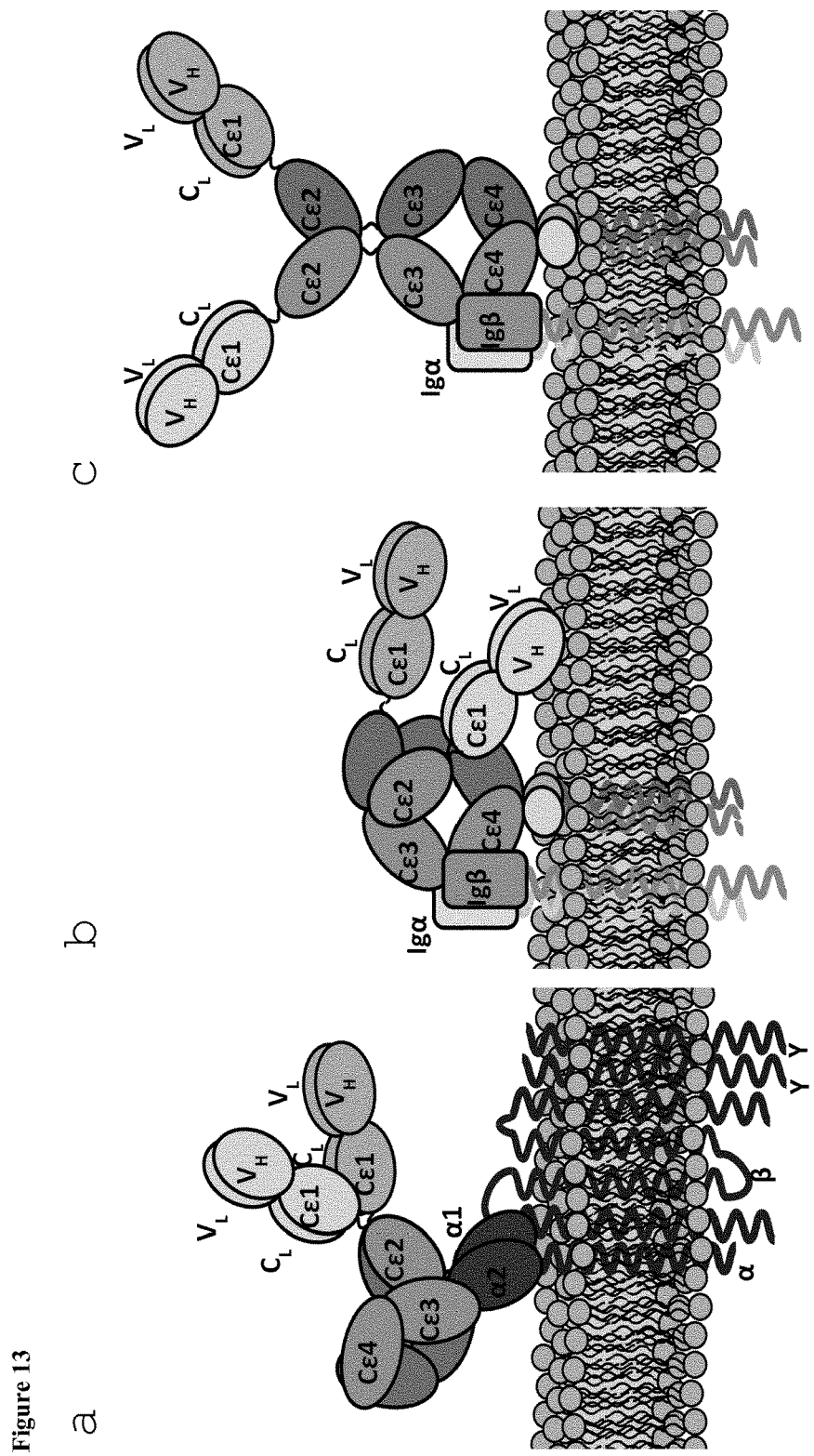

FIG. 13 Schematic representation of the structure of the entire IgE molecule in two different biological contexts. a, When bound to the high affinity receptor, IgE-Fc is acutely and rigidly bent, resulting in the Fab arms disposed for allergen recognition and crosslinking IgE (chain A and chain B), and receptor are shown. b, As part of the BCR, a rigidly bent IgE molecule would direct the Fab arms towards the membrane, making it difficult to see how allergen recognition could occur. The extra membrane-proximal domains of mIgE are indicated as small spheres between Cε4 and the trans-membrane domain. Igαβ, the BCR accessory proteins, are also shown. c, An extended conformation of IgE, would position the Fab arms optimally for allergen recognition in the BCR. While such a conformation is only transient when IgE-Fc is unbound in solution, Igαβ, may function to stabilize the extended structure.

FIG. 14 Shows the polynucleotide and amino acid sequences for Fab7.

EXAMPLE 1

Antibody-Enabled Small-Molecule Fragment Screening and Elaboration

Antibody constraint of target proteins in specific biologically relevant conformations (the inactive state is illustrated in FIG. 1) using antibodies with a low dissociation rate constant of less than $1 \times 10^{-4}$ s$^{-1}$ may enable the binding of small-molecule fragments (shown) that would otherwise not be able to gain a foothold on a target protein. This technology is particularly well suited to small-molecule fragment screening, as the throughput matches the relatively small numbers of fragments in libraries (typically ~1,000-10,000).

a) In a surface plasmon resonance-based fragment screen, an antibody or antibody fragment is immobilized on the surface of a chip. The target protein is captured by the antibody and presented in a specific conformation to enable small-molecule fragments to bind from the solution phase. In the example that is shown, the antibody is holding the target protein in an inactive conformation and revealing previously unknown structural features that are potentially suitable for targeting with small molecules.

b) Libraries of low-molecular-mass compounds are consecutively passed over the antibody-constrained target protein. As the target protein has a low dissociation rate from the antibody, there would be very little loss of mass, and hence signal, from the chip surface (owing to the release of the protein); this would enable the specific binding of any fragments (represented by the square) to be measured. In addition, fragments tend to have fast dissociation rates from proteins, thus alleviating the requirement for the regeneration of the target after every cycle.

c) Antibody constraint could continue to be used during the early stages of fragment elaboration, as the potency of initial fragment hits would be low (affinities are likely to be in the high micromolar or low millimolar range), and early analogues of the initial hits would probably still be insufficiently potent to constrain the protein independently from the antibody.

d) Once sufficient potency has been designed into the small molecule through iterative rounds of medicinal chemistry, binding will become independent of antibody constraint, and the small molecule will mimic aspects of the biological function of the antibody.

EXAMPLE 2

Analysis of IgE

Antibody Generation

Anti-human IgE antibodies were generated using UCB proprietary core antibody discovery technology. The isolated V-region genes were sub cloned in the human IgG$_1$ Fab format for subsequent expression and purification. The Fab was transiently expressed in CHO cells and purified by Protein G affinity chromatography followed by size exclusion chromatography. The ability of the Fab to inhibit the binding of IgE (Uniprot reference P01854) to FcεRIα (Uniprot reference P12319) was determined by surface plasmon resonance.

Protein Expression and Purification

IgE-Fc(N265Q,N371Q) secreted from a stable NS-0 cell line was purified from tissue culture supernatant by cation exchange. Briefly, supernatant was buffer-exchanged into 50 mM sodium acetate pH 6.0, 75 mM sodium chloride and loaded onto a SPHP cation exchange column (GE Healthcare). IgE-Fc(N265Q,N371Q) was eluted with a 10 CV gradient into 50 mM sodium acetate, pH 6.0, 1 M sodium chloride. Eluted fractions were pooled, concentrated and further purified by size exclusion chromatography on a Superdex S200 column (GE Healthcare) in PBS, pH 7.4.

Fab Expression and Purification

Anti-IgE Fab was expressed by transient transfection in CHOS cells. Cells were cultured in CD-CHO with the addition of 10 mM Glutamine at a temperature of 37° C. with 8% $CO_2$ and a rotation of 140 rpm. Transfection was carried out using electroporation, $2 \times 10^8$ cells/ml were resuspended in Earles Balance Salt Solution before 400 ug of DNA was added. Cells were electroporated and then resuspended in 100 ml of CD-CHO medium and incubated for 24 hours. Incubation continued at 32° C. for 13 days and at 4 days post transfection sodium butyrate (3 mM final concentration) was added to the culture. On day 14 post-transfection, cell culture supernatants were harvested by centrifugation (400×g for 1 hour) for purification.

Fab was purified by Protein G affinity chromatograohy (GE Healthcare) and bound Fab eluted in 100 mM glycine-HCl, pH 2.7 and fractions neutralized with $\frac{1}{25}^{th}$ fraction volume of 2 M Tris-HCl pH 8.5. Fab was further purified by size exclusion chromatography on a Superdex 5200 column (GE Healthcare) in crystallography buffer (25 mM Tris-HCl, 20 mM NaCl, 0.05% (w/v) $NaN_3$, pH 7.5).

IgE-Fc:Fab complex was prepared by mixing anti-IgE Fab with IgE-Fc at a 2:1 molar ratio and purification to homogeneity by size exclusion chromatography as described above.

Crystallisation

Sitting drop vapour diffusion crystallization experiments were set up with a protein complex concentration of 5 mg/mL in 20 mM NaCl, 25 mM Tris-HCl pH 7.5, and 0.05% sodium azide. Crystals were grown at 18° C. using 12-22% PEG3350, 0.25 M sodium citrate, and 0.1 M Bis-Tris Propane pH 7.5-9.0 as precipitant. Drops were microseeded using crystals grown under identical crystallization conditions in earlier trials. Crystals were flash cooled in liquid nitrogen using 4M trimethylamine N-oxide as cryoprotectant.

Data Collection and Structure Determination

Diffraction data were collected at beamline I03, Diamond Light Source (Harwell, U.K.). Xia2 was used to index, integrate, and merge data to 2.9 Å resolution. The phases were solved using Phaser molecular replacement[20]. To generate the Fab search model the RCSB PDB protein sequence search engine was used to find 3 QHZ, from which the non-conserved residues were removed using CHAIN-SAW[21,22]. IgE-Fc search models were generated by splitting the coordinates from the high resolution IgE-Fc structure (PDB 2WQR), into Cε2 and Cε3-4 fragments. The location of each of the molecules in the asymmetric unit were identified in sequential searches: $Fab^1$ was identified first, followed by $(C\varepsilon 3\text{-}4)_2$, $Fab^1$, and finally $(C\varepsilon 2)_2$. The structure was initially rebuilt using the autobuild wizard of PHENIX[23], and then refined using iterative cycles of PHENIX[23] and REFMAC[24], with 5% of reflections set aside from refinement for calculation of $R_{free}$. Between refinement cycles, the structure was manually built into $2F_o\text{-}F_c$ and $F_o\text{-}F_c$ electron density maps using COOT[25]. Composite omit maps were generated using the autobuild wizard in PHENIX to prevent model bias[23]. Carbohydrate and water molecules were manually built into the structure. MolProbity[26] and CARP[27] were used to assess protein and carbohydrate geometry respectively. PISA[28], CONTACT, and NCONT as part of the CCP4 program suite[29] were used for analysis of protein-protein interfaces, and DynDom[30] was used to calculate the domain motion involved in the conformational changes. Structure morphs for movies were calculated using the UCSF CHIMERA package[31], and videos made using PyMOL.

Enhanced Molecular Dynamics

The bent crystal structure (PDB 2WQR) was used as the starting point for molecular dynamic simulation, after adding missing atoms and picking protonation states with Maestro (Schrodinger LLC). The AMBER ff99SB-ildn and GLYCAM force fields were used for protein and carbohydrate respectively. The structure was solvated in a dodecahedron, such that no protein atom was within 1.4 nm of the edge, and monoatomic ions were added to a salt concentration of 0.15 M.

Simulations were carried out with GROMACS 4.5.3 patched with Plumed-1.3. In the initial stages of temperature equilibration, a 1 fs time step was used, which was increased to 2 fs for the remainder of the simulation. Particle mesh Ewald was used for long range electrostatics along with 1 nm cut-offs for Coulomb and Lenard-Jones potential functions. A preliminary 500 ns unbiased simulation was used to extract two collective variables (CVs) through principle component analysis (PCA). Only every other α-carbon was included in the PCA CVs. An exploratory metadynamics simulation then used these PCA CVs to explore unbending for ~400 ns Gaussian's of height 8 kJ/mol and sigma of 0.06 nm added every 4 ps. This exploratory metadynamics run then provided new PCA CVs for a final metadynamics simulation which converged after more than 1200 ns.

Isothermal Titration Calorimetry

Experiments were carried out using a Microcal iTC200 calorimeter (GE Healthcare) at 20° C. in PBS buffer pH 7.4. Depending on the final ratio required, 25-30 μM of protein was used in the calorimeter cell and 10-20 fold higher concentrations were used in the syringe. The number and volume of injections were varied as appropriate. Heats of dilution were subtracted from the data before analysis. When Analyses were carried out using MicroCal Origin, using a 1:1 binding model when IgE-Fc or Fcε3-4 was titrated into Fab, or a sequential 1:1 binding model when Fab was titrated into IgE-Fc or Fcε3-4.

Stopped Flow Fluorescence

Experiments were carried out using a Chirascan Plus (Applied Photophysics Ltd) with a stopped-flow attachment at 20° C. in PBS buffer pH 7.4 and with pseudo-first order protein concentrations varied as required. Fluorescence was excited at 280 nm (1 nm slit width) and emitted fluorescence above 305 nm detected with a long-band pass. 6-10 runs were averaged for each experiment. Data were collected and analyzed using supplied software according to the manufacturer's instructions. Experimental transients were fitted either to single-exponential (Eq.1; [IgE-Fc] or [Fcε3-4]> [Fab] and only $Fab^1$ binding observable) or double-exponential (Eq.2; [Fab]>[IgE-Fc] or [Fcε3-4] and binding of both $Fab^1$ and $Fab^2$ observable) equations:

$$F = \Delta F_1 \exp(-k_{obs1} t) + F_e \quad \text{(Eq.1)}$$

$$F = \Delta F_1 \exp(-k_{obs1} t) + \Delta F_2 \exp(-k_{obs2} t) + F_e \quad \text{(Eq.2)}$$

where F is the observed fluorescence, $\Delta F_n$ is the fluorescence amplitude change for the nth transient, $k_{obsn}$ is the pseudo-first order rate constant for the nth step and $F_e$ is the end-point fluorescence. The bimolecular association rate constants for Fab$^1$ ($k_{+1}$) and Fab$^2$ ($k_{+2}$) binding were determined by fitting the linear concentration dependences of $k_{obs1}$ and $k_{obs2}$ to Eq. 3:

$$k_{obsn} = k_{+n}[\text{ligand}] + k_{-n} \quad (\text{Eq.3})$$

where $k_{obsn}$ is the pseudo-first order rate constant for the nth transient at the ranges of ligand concentrations used, is the association rate constant for the nth Fab binding event and $k_{-n}$ is the dissociation rate constant for the nth Fab binding.

TABLE 1

ITC & stopped flow analysis of the interaction between Fab & IgE-Fc or Fcε-4

|  | $K_d$ ITC (μM) | $k_{on}$ (M$^{-1}$s$^{-1}$) | $k_{off}$ (s$^{-1}$) | $k_{on2}$ (M$^{-1}$s$^{-1}$) | $k_{off2}$ (s$^{-1}$) |
|---|---|---|---|---|---|
| 1Fab\|1IgE-Fc | 0.070 | 6.7 (±0.2) × 10$^5$ | n/m | — | — |
| 2Fab\|1IgE-Fc | 0.076, 1.5 | 3.5 (±0.2) × 10$^5$ | 3.2 (±0.1) | 1.2 (±0.2) × 10$^5$ | n/m |
| 1Fab\|1Fcε3-4 | 0.090 | 1.0 (±0.1) × 10$^6$ | n/m | — | — |
| 2Fab\|1Fcε3-4 | 0.034, 0.98 | 1.0 (±0.1) × 10$^6$ | 0.95 (±0.2) | 3.7 (±0.3) × 10$^5$ | n/m | n/m not measurable, too slow to measure.

Fret

Intramolecular FRET was carried out using IgE-Fc (E289C)_BirA (IgE-Fc with the BirA recognition motif added to the C-terminus and biotinylaated according to the manufacturer's instructions (Avidity)) labeled with thiol reactive terbium chelate (Invitrogen) and streptavidin labeled with amine reactive Alexa488 (Invitrogen), each according to the manufacturer's instructions. Terbium labeled IgE-Fc and Alexa488 labeled streptavidin were mixed in equi-molar ratios (FAC 25 nM) with anti-IgE Fab titrated from 30 uM in PBS and incubated for 120 minutes at room temperature. FRET was measured on an Analyst LJL-HT (excitation 200 nm, emission 485 and 520 nm, each at 10 nm slit width) and plotted as a function of Fab concentration.

The present inventors have illustrated the binding of a Fab fragment (referred to herein as Fab7 (FIG. 14 SEQ ID NO: 2 and 4) with IgE-Fc and resolved the crystal structure at 2.9 Å resolution.

Crystal structure data collection and refinement statistics are provided below:

| Data collection | Fab$^1$\|Fc\|Fab$^2$ |
|---|---|
| Space group | P2$_1$2$_1$2$_1$ |
| Cell dimensions | |
| a, b, c (Å) | 84.59, 100.81, 219.68 |
| α = β = γ (°) | 90.0 |
| Resolution (Å) | 2.91 (67.01-2.91) |
| R$_{merge}$ | 0.055 (0.796) |
| I/σI | 18.4 (3.0) |
| Completeness (%) | 99.7 (99.2) |
| Redundancy | 3.0 (3.1) |
| Refinement | |
| Resolution (Å) | 2.91 (2.98-2.91) |
| No. reflections | 41910 |
| R$_{work}$/R$_{free}$ | 0.237/0.285 |
| No. atoms | 11712 |

-continued

| Protein | 11541 |
|---|---|
| Non-protein | 122$^a$ |
| Water | 49 |
| B-factors (Å$^2$) | |
| Protein | 103.8 |
| Non-protein | 110.9$^a$ |
| Water | 88.4 |
| R.m.s. deviations | |
| Bond lengths (Å) | 0.010 |
| Bond angles (°) | 1.566 |

-continued

| Ramachandran | |
|---|---|
| Favoured (%) | 93.6 |
| Outliers (%) | 0.2 |

Values in parentheses are for the highest-resolution shell.
$^a$Carbohydrate.

To explore the range of conformations that IgE can adopt, particularly with regard to the Cε2 domains, a novel IgG antibody that binds to IgE-Fc and inhibits its interaction with FcεRIα was generated, and the crystal structure of the complex solved using a Fab fragment of the IgG.

Remarkably, the IgE-Fc adopts a totally extended conformation, with two Fab molecules bound, one on each side of the almost perfectly symmetrical IgE-Fc complex (Fab$^1$|IgE-Fc|Fab$^2$, FIGS. 2b and 2c). Compared with the structure of IgE-Fc alone, the molecule has undergone a drastic "unbending" of 120° (FIGS. 2a and 2c), losing completely the extensive intra-molecular interface between the Cε2 and Cε3-Cε4 domains. This unbending derives largely from movements in the Cε2-Cε3 linker region, in particular residues P333, R334 and G335, which act as mechanical hinges. While the Cε2 domains display the greatest structural change, the Cε3 domains also undergo considerable movement. Conformational flexibility has been seen in a number of structures of the Fcε3-4 sub-fragment of IgE-Fc, with the Cε3 domains described as "open" or "closed" (together with a "swinging" of one Cε3 domain relative to the other, see FIG. 6)$^{11}$. In the bent structure of IgE-Fc alone, one Cε3 is "open" (chain B) and one is "closed" (chain A), whereas in the extended conformation of IgE-Fc revealed here, both Cε3 domains adopt an "open" conformation (FIG. 7). Cε3$^A$ thus undergoes much more of a change than Cε3$^B$ upon Fab binding, with a Cε3-Cε4 hinge movement of 15°. The (Cε4)$_2$ pair are unchanged upon complex formation. Such is the symmetry of the IgE-Fc in the complex that the local two-fold axes of all three domain pairs are virtually coincident.

As a result of this symmetry the two Fab interfaces are structurally equivalent (each ~1400 Å²), mainly involving contact of the Fab heavy and light chains with Cε3, but with a small interaction with Cε2 (FIG. 8a). Each Fab molecule principally contacts a single IgE-Fc chain (Fab¹ to IgE-Fc^A and Fab² to IgE-Fc^B), with the exception of a 315 Å² interface with the Cε2-Cε3 linker region (including S331 and N332) of the other IgE-Fc chain (FIGS. 8b and c). The 'hot spot' of the Fab binding surface on IgE-Fc appears to be the Cε3 residue R393, which protrudes into a pocket at the interface of the heavy and light chains of the Fab7 molecule (FIG. 8d) forming a salt bridge (to D121") and hydrogen bonds (to E109^L and N54^L; FIGS. 8e and f). The adjacent Cε3 residues also contribute extensively (FIG. 8d). Strikingly however, only one Fab-binding interface (IgE-Fc^A) is accessible in the crystal structure of free IgE-Fc; the second site (on IgE-Fc^B) is occluded by the Cε2 domains that fold back and make contact in this region. Residue R393 of IgE-Fc^A is thus a likely candidate for initial engagement of Fab¹ binding.

The interaction between IgE-Fc and FcεRIα is extraordinarily tight ($K_d \approx 0.1$ nM)¹ and involves binding at two sub-sites, one on each Cε3 domain (FIG. 9a)[7,12]. The Fab molecule described here achieves inhibition of this interaction by both an allosteric and a direct steric blocking mechanism. The structures of both receptor-binding sub-sites are drastically altered in the extended form of IgE-Fc (FIG. 9). In sub-site 1 on IgE-Fc^A, R334 forms a critically important salt bridge with FcεRIα, but this residue is part of the hinge involved in the movement of the Cε2 domain pair, and undergoes considerable rearrangement compared to both free and receptor-bound IgE-Fc; it is no longer in a position to engage in FcεRIα binding. Similarly, the second sub-site on IgE-Fc^B involves a proline (P426 of Cε3^B) sandwiched between two tryptophan residues (W87 and W110 of FcεRIα), but this proline moves 6 Å away from its receptor-bound conformation in the Fab complex. In addition to this conformational disruption of the FcεRIα binding sub-sites, the new positions of the Cε2 domains in the Fab complex (and one of the Fabs also) overlap spatially with the location of the receptor, even though Fab and FcεRIα do not compete for binding to the same IgE-Fc residues (FIG. 9c).

Whilst the structure of the Fab¹|IgE-Fc|Fab² complex reveals that an extended conformation of IgE-Fc is feasible, the important question is whether it is just a consequence of Fab binding, or whether such a conformation exists in solution as an intrinsic property of IgE. Metadynamics, an enhanced molecular dynamics method, has been used to produce a detailed atomistic simulation of the IgE-Fc unbending process[13-16]. The resultant free-energy surface is calculated and presented in terms of the two principal components of the molecule's unbending dynamics (FIG. 3a). The most stable conformation is clearly the bent conformation seen in the crystal structure⁶ (FIG. 3b conformation 1). A partially bent conformation is 13 kJ/mol less stable than the bent conformation (FIG. 3b conformation 2). The most stable extended conformation (FIG. 3b conformation 3), is ~6 kJ/mol less stable than the dominating bent state. These free-energy data clearly suggest a dynamic pathway from the bent to the fully extended conformation, from which the Cε2 domains could then fold back onto the other side of the Cε3-Cε4 domains, completing a "flip" from one bent conformation to the other. A conformation very close to the symmetrically extended structure seen in the Fab complex (FIG. 3b conformation 4) may be close to the saddle point for this flip. This is entirely consistent with the experimental observation that the bent conformation predominates in solution[4,5,10].

One way to establish experimentally that IgE-Fc adopts an extended structure as it flips between two bent conformations, is to determine the number of Fab binding sites that are available for binding: if rigidly and exclusively bent, only one site will initially be accessible, but if it can flip, then two sites are accessible. We therefore studied the interaction between Fab and IgE-Fc by isothermal titration calorimetry (ITC) and compared with the binding to Fcε3-4 which, lacking the Cε2 domains, always has two accessible sites. The results for both IgE-Fc and Fcε3-4 are similar, and show that both display two accessible sites (a stoichiometry of one IgE-Fc site or Fcε3-4 site to one Fab; FIGS. 4a & b), thus supporting the model in which IgE-Fc flips. The $K_d$ values for Fab binding to IgE-Fc and Fcε3-4 were found to be 70 nM and 90 nM respectively (FIGS. 4a & b; Table 1), but in order to distinguish between the affinities for binding of the first Fab with binding of the second, the ITC experiment was then conducted by titrating Fab into either IgE-Fc or Fcε3-4 (FIGS. 4c & d). This revealed two $K_d$ values for IgE-Fc of 76 nM and 1.5 μM at stoichiometries of Fab:IgE-Fc of 1:1 and 2:1 respectively (with similar values for Fcε3-4; Table 1); the second Fab clearly binds more weakly than the first.

In order to investigate the assembly mechanism of the Fab¹|IgE-Fc|Fab² complex, we used stopped-flow kinetic analysis, utilising the intrinsic tryptophan fluorescence of the unlabelled proteins to monitor binding. When IgE-Fc (or Fcε3-4 for comparison) was in excess over Fab, thus restricting the stoichiometry of the Fab:IgE-Fc (or Fcε3-4) complex to 1:1, a single binding event was observed (FIG. 10). This binding event has a fast association rate constant and very slow dissociation, consistent with the ITC results (Table 1). When repeated with Fab in excess over IgE-Fc, two-step binding was observed (FIG. 10), with both binding events demonstrating linear concentration dependences (FIG. 11). Similar results were observed for both IgE-Fc and Fcε3-4 (FIGS. 10 and 11), and are consistent not only with Fab¹ binding faster than Fab², but also the difference in affinities of the two sites determined by ITC.

In envisaging the mechanism of formation of the Fab¹|IgE-Fc|Fab² complex, the question remains: does binding of Fab¹ trap IgE-Fc in an extended conformation or can it still flex between the extended and bent structures? These two alternatives can be discriminated using intra-molecular FRET (Förster Resonance Energy Transfer). We recently demonstrated how this could be used to observe in solution the extent of bending in IgE-Fc upon ligand binding[10]. Here, we titrated Fab into IgE-Fc labelled with donor and acceptor fluorophores in the Cε2 and Cε4 domains respectively, to observe whether unbending (detected by a decrease in the FRET signal) occurs upon engagement of Fab¹ or Fab². The decrease in FRET clearly occurred only upon binding of Fab² to form the Fab¹|IgE-Fc|Fab² complex (FIG. 12).

The structural and molecular dynamics simulation data imply, and the solution studies demonstrate, that IgE-Fc can undergo a Cε2 flip and that extended conformations of IgE-Fc exist in solution. FIG. 5 depicts the formation of the Fab¹|IgE-Fc|Fab² complex.

1. IgE-Fc is predominantly bent in solution (consistent with X-ray and neutron scattering⁵ and FRET[10]), but transiently adopts conformations such as those identified in the molecular dynamics simulation with the (Cε2)₂ domain pair spontaneously flipping from one side of the molecule to the other. 2. Fab¹ engages IgE-Fc on either side of the molecule.

3. With Fab[1] bound, the mobility of IgE-Fc is restricted, but it is still capable of flexing between the extended and bent conformations. The latter predominates and is observed by FRET. 4.

When IgE-Fc is transiently in the extended conformation, Fab[2] engages and completes the Fab[1]|IgE-Fc|Fab[2] complex.

We have now shown that this can indeed occur, which implies that it will also be true for the whole IgE molecule since the Fab regions are not expected to interfere with the IgE-Fc[10]. That IgE has evolved to incorporate a compact, rigid conformation within an ensemble of extended, flexible structures, may be understood in terms of its biological role. IgE recognises allergens in two very different contexts, either bound to FcεRI on effector cells (such as mast cells) or in its membrane-bound form as part of the B cell receptor (BCR). The existence of the (even more) acutely and rigidly bent receptor-bound IgE molecule can be rationalised, since it presents the Fab arms in such a way as to facilitate cross-linking by allergen[10] (FIG. 13a). However, it is difficult to see how a rigidly bent IgE molecule could function in allergen recognition in the BCR, since the Fab arms would be directed towards the membrane (FIG. 13b). An extended structure, perhaps stabilised by accessory cell-surface molecules (FIG. 13c), would dispose the Fab arms optimally. It is intriguing that IgM, the most primitive antibody, has Cμ2 domains homologous to Cε2. In the absence of any crystallographic data on IgM, models for the IgM BCR, soluble pentameric IgM, and conformational changes within these structures (for example to regulate complement activation) have been proposed[17-19]. These models and their mechanistic implications may now be revisited.

EXAMPLE 3

Small Molecule Fragment Screening

Further antibodies were generated which were able to inhibit IgE binding to its receptor FcεRIα. Of these, six were all able to unbend IgE to different degrees as determined by FRET analysis conducted using the method described in Example 2 above for Fab7. See Table 2 and FIG. 12. The affinities of these six antibodies were also determined (Table 3).

TABLE 2

Fret data for Antibodies 1967, 1992, 1970, 1998, 1981, 1982 and Fab7

| | | 1967 | | | | 1992 | |
|---|---|---|---|---|---|---|---|
| [Fc]/[Fab] | [Fab] nM | mean | sd | [Fc]/[Fab] | [Fab] nM | mean | sd |
| 120 | 3000 | 57.175 | 1.705628 | 120 | 3000 | 11.7 | 2.706782 |
| 40 | 1000 | 55.3 | 1.773885 | 40 | 1000 | 10.125 | 1.676057 |
| 13.32 | 333 | 53.575 | 0.838153 | 13.32 | 333 | 8.35 | 1.915724 |
| 4.44 | 111 | 50.4 | 1.852926 | 4.44 | 111 | 9.675 | 1.939716 |
| 1.4812 | 37.03 | 25.5 | 2.472516 | 1.4812 | 37.03 | 9.2 | 1.71075 |
| 0.492 | 12.3 | 3.4 | 2.496664 | 0.492 | 12.3 | 4.15 | 2.048577 |
| 0.176 | 4.4 | 0 | 1.984943 | 0.176 | 4.4 | 0.975 | 1.668083 |
| 0.0548 | 1.37 | 1.15 | 1.292285 | 0.0548 | 1.37 | 0.525 | 1.499722 |
| 0.018 | 0.45 | −0.7 | 1.042433 | 0.018 | 0.45 | 0.775 | 2.760888 |
| 0.00608 | 0.152 | −0.125 | 2.375395 | 0.00608 | 0.152 | 2.025 | 3.1106 |

| | 1970 | normalised FRET | | | 1998 | normalised FRET | |
|---|---|---|---|---|---|---|---|
| [Fab]/[Fc] | [Fab] nM | mean | sd | [Fab]/[Fc] | [Fab] nM | mean | sd |
| 120 | 3000 | 9.75 | 2.185559 | 120 | 3000 | 9.7 | 1.197219 |
| 40 | 1000 | 8.625 | 0.537742 | 40 | 1000 | 10.325 | 2.28382 |
| 13.32 | 333 | 8.325 | 1.436141 | 13.32 | 333 | 8.575 | 2.223173 |
| 4.44 | 111 | 11.9 | 0.984886 | 4.44 | 111 | 10.05 | 1.913984 |
| 1.4812 | 37.03 | 9.6 | 2.56645 | 1.4812 | 37.03 | 6.15 | 1.181807 |
| 0.492 | 12.3 | 6.15 | 0.556776 | 0.492 | 12.3 | 5.9 | 1.679286 |
| 0.176 | 4.4 | 4.6 | 2.446767 | 0.176 | 4.4 | 1.075 | 1.65 |
| 0.0548 | 1.37 | 1.3 | 2.369247 | 0.0548 | 1.37 | 1.4 | 3.182242 |
| 0.018 | 0.45 | 1.45 | 2.556691 | 0.018 | 0.45 | 0.35 | 1.774824 |
| 0.00608 | 0.152 | 0.2 | 2.836665 | 0.00608 | 0.152 | 1.325 | 2.043486 |

| | 1981 | normalised FRET | |
|---|---|---|---|
| [Fab]/[Fc] | [Fab] nM | mean | sd |
| 120 | 3000 | 9.725 | 0.818026 |
| 40 | 1000 | 10.125 | 1.178629 |
| 13.32 | 333 | 6.55 | 1.884144 |
| 4.44 | 111 | 8.675 | 1.983893 |
| 1.4812 | 37.03 | 8.175 | 1.252664 |
| 0.492 | 12.3 | 4.1 | 2.068816 |
| 0.176 | 4.4 | 1.125 | 2.882563 |
| 0.0548 | 1.37 | 1.075 | 2.258871 |
| 0.018 | 0.45 | 1.675 | 2.232151 |
| 0.00608 | 0.152 | 1.5 | 1.267544 |

TABLE 2-continued

Fret data for Antibodies 1967, 1992, 1970, 1998, 1981, 1982 and Fab7

| | 1982 | normalised FRET | | | Fab7 | normalised FRET | |
|---|---|---|---|---|---|---|---|
| [Fab]/[Fc] | [Fab] nM | mean | sd | [Fab]/[Fc] | [Fab] nM | mean | sd |
| 120 | 3000 | 14.7 | 1.760682 | 120 | 3000 | 41.05 | 2.748939 |
| 40 | 1000 | 10.575 | 1.965324 | 40 | 1000 | 43.375 | 1.658061 |
| 13.32 | 333 | 9.375 | 1.3301 | 13.321 | 333 | 39.275 | 1.600781 |
| 4.44 | 111 | 9.2 | 2.180214 | 4.441 | 111 | 28.775 | 2.033675 |
| 1.4812 | 37.03 | 7.233333 | 2.074448 | 1.4812 | 37.03 | 9.675 | 2.030394 |
| 0.492 | 12.3 | 4.475 | 3.265348 | 0.492 | 12.3 | 2 | 2.27303 |
| 0.176 | 4.4 | 2.075 | 1.857193 | 0.176 | 4.4 | 0.1 | 0.912871 |
| 0.0548 | 1.37 | 1.7 | 3.23213 | 0.0548 | 1.37 | 1.55 | 1.793507 |
| 0.018 | 0.45 | 1.15 | 2.556691 | 0.018 | 0.45 | 0.2 | 1.722401 |
| 0.00608 | 0.152 | 2.875 | 2.963528 | 0.00608 | 0.152 | 1 | 1.5705631 |

BIAcore Kinetics for IgE-Fc Binding to a Conformational Antibody

BIA (Biamolecular Interaction Analysis) was performed using a BIAcore T200 (GE Healthcare). Affinipure F(ab')$_2$ Fragment goat anti-rabbit IgG, Fc fragment specific (Jackson ImmunoResearch) was immobilised on a CM5 Sensor Chip via amine coupling chemistry to a capture level of ≈4400 response units (RUs). HBS-EP buffer (10 mM HEPES pH 7.4, 0.15 M NaCl, 3 mM EDTA, 0.05% Surfactant P20, GE Healthcare) was used as the running buffer with a flow rate of 10 μL/min. A 10 μL injection of a conformational antibody (IgG1) at 0.5 μg/mL was used for capture by the immobilised anti-rabbit IgG-F(ab')$_2$. IgE-Fc was passed over the captured conformational antibody at concentration of 50 nM at a flow rate of 30 4/min. The surface was regenerated by 10 μL injection of 50 mM HCl, followed by a 10 μL injection of 5 mM NaOH and 10 μL injection of 50 mM HCl at a flowrate of 10 μL/min. Background subtraction binding curves were analysed using the T200evaluation software (version 1.0) following standard procedures. Kinetic parameters were determined from the fitting algorithm.

TABLE 3

| Antibody | ka (1/Ms) | kd (1/s) | KD (M) | KD (pM) |
|---|---|---|---|---|
| CA062_01967.0_P42 | 3.28E+06 | 2.42E−05 | 7.39E−12 | 7.39 |
| CA062_01970.0_P42 | 1.60E+06 | 1.39E−05 | 8.71E−12 | 8.71 |
| CA062_01981.0_P42 | 2.99E+06 | 1.13E−05 | 3.78E−12 | 3.78 |
| CA062_01982.0_P42 | 1.38E+06 | 7.95E−06 | 5.76E−12 | 5.76 |
| CA062_01992.0_P42 | 1.26E+06 | 6.69E−06 | 5.31E−12 | 5.31 |
| CA062_01998.0_P42 | 3.56E+06 | 4.75E−06 | 1.33E−11 | 13.35 |

Average of 2 Determinations

Surface Plasmon Resonance Method for Detecting Compound Binding to Antibody Constrained Conformations of IgE, Unconstrained IgE and Free Antibody Here six antibodies "capturing" IgE in varying conformational states were studied. The single point binding assay was performed on a Biacore 4000 hydrodynamically addressed to permit immobilisation of proteins to relevant detection spots within four flow cells.

Initially antibody pairs were immobilised on each side of the flow cell i.e. Antibody A on detection spots 1 & 2 and Antibody B on spots 4 & 5.

Conditions Used for the Direct Immobilization of IgE-Fc or Anti-IgE Antibody (BIAcore 4000)

IgE-Fc fragment was diluted to a final concentration of c=40 μg/ml using 10 mM sodium acetate buffer pH=5.0 (GE Healthcare). IgE-Fc was immobilised on a CM5 sensor chip via amine coupling chemistry. A 50 ul injection of IgE-Fc resulted in a immobilisation level of ~12000 responsive units (RUs) and 10 mM sodium acetate with 150 mM NaCl, pH=5.0 was used as the running buffer with a flow rate of 10 μL/min.

The following Table summarises immobilisation conditions for each antibody:

TABLE 4

Buffers employed for all antibodies (10 mM sodium acetate pH 5.0 immobilisation buffer and 10 mM sodium acetate + 150 mM NaCl pH 5.0 running buffer)

| Antibody | Conc | Flow rate | Contact time | Target level |
|---|---|---|---|---|
| Ab_1982 | 25 ug/ml | 10 ul/min | 10 min | 8000-11000 RU |
| Ab_1992 | 25 ug/ml | 10 ul/min | 10 min | 8000-11000 RU |
| Ab_1970 | 40 ug/ml | 10 ul/min | 10 min | 8000-11000 RU |
| Ab_1967 | 40 ug/ml | 10 ul/min | 10 min | 8000-11000 RU |
| Ab_1981 | 25 ug/ml | 10 ul/min | 7 min | 8000-11000 RU |
| Ab_1998 | 25 ug/ml | 10 ul/min | 7 min | 8000-11000 RU |

Following immobilisation, the antibody surface is conditioned with the following pulse sequence; 60 sec 40 mM HCl, 20 sec NaOH and 60 sec HCl (flow rate 10 ul/min). IgE was captured to form Ab_IgE complex on spots 1 and 5 at a concentration 50 nM in 1×HBS-EP (GE Healthcare) buffer (flow rate 30 ul/min), running buffer 1×HBS-EP (GE Healthcare). The IgE capture process was repeated until the desired level achieved i.e 6000-8000RU. Spots 4 and 5 were antibody alone, no IgE captured.

For the Ab_1998 a further stabilisation step was required; immediately after IgE capture, EDC/NHS mix was injected over the relevant spot containing the Ab_1998+IgE complex for 30 sec at 30 ul/min followed by injection of Ethanolamine 180 sec at 30 ul/min.

Following capture the surface was equilibrated in the compound screening buffer, 1×HBS-P+5% DMSO overnight. Compounds were then screened at 250 uM in 1×HBS-P+5% DMSO final, injected for 60 seconds contact time switching to buffer flow 180 secs to measure dissociation.

In a parallel experiment the same compounds were passed over immobilised IgE-Fc (i.e. in the absence of antibody) using the same conditions.

The total number of compounds screened was 1,933 all with a molecular weight of less than 300. 29 compounds were identified that bound the antibody constrained IgE but not the unbound IgE. An example of a compound that bound the antibody constrained protein included; compound 1 with MW (molecular weight)=214, AlogP=−1.1, PSA (polar surface area)=63; compound 2 with MW=193, AlogP=−1.9, PSA=70; and compound 3 with MW=123, AlogP=−1.0, PSA=50.

REFERENCES

1. Gould, H. J. & Sutton, B. J. IgE in allergy and asthma today. *Nature Reviews Immunology* 8, 205-217 (2008).
2. Padlan, E. A. & Davies, D. R. A model of the Fc of Immunoglobulin-E. *Molecular Immunology* 23, 1063-1075 (1986).
3. Davis, K. G., Glennie, M., Harding, S. E. & Burton, D. R. A model for the solution conformation of rat IgE. *Biochemical Society Transactions* 18, 935-936 (1990).
4. Zheng, Y., Shopes, B., Holowka, D. & Baird, B. Conformations of IgE bound to its receptor Fc-Epsilon-RI and in solution. *Biochemistry* 30, 9125-9132 (1991).
5. Beavil, A. J., Young, R. J., Sutton, B. J. & Perkins, S. J. Bent domain-structure of recombinant human IgE-Fc in solution by x-ray and neutron-scattering in conjunction with an automated curve-fitting procedure. *Biochemistry* 34, 14449-14461 (1995).
6. Wan, T. et al. The crystal structure of IgE Fc reveals an asymmetrically bent conformation. *Nature Immunology* 3, 681-686 (2002).
7. Holdom, M. D. et al. Conformational changes in IgE contribute to its uniquely slow dissociation rate from receptor Fc epsilon RI. *Nature Structural & Molecular Biology* 18, 571-U187 (2011).
8. McDonnell, J. M. et al. The structure of the IgE C epsilon 2 domain and its role in stabilizing the complex with its high-affinity receptor Fc epsilon R1 alpha. *Nature Structural Biology* 8, 437-441 (2001).
9. Holgate, S. T., Djukanovic, R., Casale, T. & Bousquet, J. Anti-immunoglobulin E treatment with omalizumab in allergic diseases: an update on anti-inflammatory activity and clinical efficacy. *Clinical and Experimental Allergy* 35, 408-416 (2005).
10. Hunt, J. et al. A fluorescent biosensor reveals conformational changes in human Immunoglobulin E Fc: Implications for mechanisms of receptor binding, inhibition, and allergen recognition. *The Journal of Biological Chemistry* 287, 17459-70 (2012).
11. Wurzburg, B. A. & Jardetzky, T. S. Conformational flexibility in Immunoglobulin E-Fc(3-4) revealed in multiple crystal forms. *Journal of Molecular Biology* 393, 176-190 (2009).
12. Garman, S. C., Wurzburg, B. A., Tarchevskaya, S. S., Kinet, J. P. & Jardetzky, T. S. Structure of the Fc fragment of human IgE bound to its high-affinity receptor Fc epsilon RI alpha. *Nature* 406, 259-266 (2000).
13. Barducci, A., Bussi, G. & Parrinello, M. Well-tempered metadynamics: a smoothly converging and tunable free-energy method. *Physical Review Letters* 100, 020603-020603 (2008).
15. Crespo, Y., Marinelli, F., Pietrucci, F. & Laio, A. Metadynamics convergence law in a multidimensional system. *Physical Review E* 81(2010).
16. Barducci, A., Bonomi, M. & Parrinello, M. Metadynamics. *Wiley Interdisciplinary Reviews-Computational Molecular Science* 1, 826-843 (2011).
17. Perkins, S. J., Nealis, A. S., Sutton, B. J. & Feinstein, A. Solution structure of human and mouse Immunoglobulin M by synchrotron X-ray scattering and molecular graphics modelling. A possible mechanism for complement activation. *Journal of Molecular Biology* 221, 1345-66 (1991).
18. Czajkowsky, D. M. & Shao, Z. The human IgM pentamer is a mushroom-shaped molecule with a flexural bias. *Proceedings of the National Academy of Sciences of the United States of America* 106, 14960-5 (2009).
19. Tolar, P., Sohn, H. W., Liu, W. & Pierce, S. K. The molecular assembly and organization of signaling active B-cell receptor oligomers. *Immunological Reviews* 232, 34-41 (2009).
20. McCoy, A. J. et al. Phaser crystallographic software. *Journal of Applied Crystallography* 40, 658-674 (2007).
21. Schwarzenbacher, R., Godzik, A., Grzechnik, S. K. & Jaroszewski, L. The importance of alignment accuracy for molecular replacement. *Acta Crystallographica Section D-Biological Crystallography* 60, 1229-1236 (2004).
22. Stein, N. CHAINSAW: a program for mutating pdb files used as templates in molecular replacement. *Journal of Applied Crystallography* 41, 641-643 (2008).
23. Adams, P. D. et al. The Phenix software for automated determination of macromolecular structures. *Methods* 55, 94-106 (2011).
24. Murshudov, G. N. et al. REFMAC5 for the refinement of macromolecular crystal structures. *Acta Crystallographica Section D-Biological Crystallography* 67, 355-367 (2011).
25. Emsley, P., Lohkamp, B., Scott, W. G. & Cowtan, K. Features and development of Coot. *Acta Crystallographica Section D-Biological Crystallography* 66, 486-501 (2010).
26. Chen, V. B. et al. MolProbity: all-atom structure validation for macromolecular crystallography. *Acta Crystallographica Section D-Biological Crystallography* 66, 12-21 (2010).
27. Lutteke, T., Frank, M. & von der Lieth, C. W. Carbohydrate Structure Suite (CSS): analysis of carbohydrate 3D structures derived from the PDB. *Nucleic Acids Research* 33, D242-D246 (2005).
28. Krissinel, E. & Henrick, K. Inference of macromolecular assemblies from crystalline state. *Journal of Molecular Biology* 372, 774-797 (2007).
29. Bailey, S. The CCP4 suite—programs for protein crystallography. Acta Crystallographica Section D-Biological Crystallography 50, 760-763 (1994).
30. Hayward, S. & Berendsen, H. J. C. Systematic analysis of domain motions in proteins from conformational change: New results on citrate synthase and T4 lysozyme. *Proteins-Structure Function and Genetics* 30, 144-154 (1998).
31. Pettersen, E. F. et al. UCSF chimera—A visualization system for exploratory research and analysis. *Journal of Computational Chemistry* 25, 1605-1612 (2004).

The invention claimed is:

1. A method of identifying compounds capable of binding to a functional conformational state of a protein of interest or protein fragment thereof, said method comprising:
   (a) binding a function-modifying antibody to the protein of interest or protein fragment thereof to provide an antibody-constrained protein or fragment, wherein the antibody has binding kinetics with the protein or fragment which are such that it has a dissociation rate constant of $1\text{-}9\times10^{-4}$ $s^{-1}$ or less,
   (b) providing a test compound which has a molecular weight of 350 Da or less,
   (c) evaluating whether the test compound of (b) binds the antibody-constrained protein or fragment, and
   (d) selecting a compound from (c) based on the ability to bind to the antibody-constrained protein or fragment.

2. The method according to claim 1, further comprising evaluating binding of an analogue of a compound selected in step (d) for binding to the antibody-constrained protein or fragment.

3. The method of claim 1, further comprising performing synthetic chemical methods to modify or elaborate a first test compound selected in step (d).

4. The method according to claim 3, wherein the modification or elaboration comprises incorporating a chemotype of a second test compound identified by a method herein.

5. The method of claim 1, wherein prior to step (a) an antibody intended for use in step (a) is pre-screened for the ability to function-modify a biological activity of the protein of interest.

6. The method of claim 1, wherein the antibody-constrained protein or fragment is used to generate three-dimensional structural information, wherein generating three-dimensional structural information comprises employing X-ray crystallography in the presence of a bound compound identified in step (c) and optionally comprising performing computation modelling based on the three-dimensional structural information obtained therefrom.

7. The method of claim 1, wherein the antibody is an allosteric antibody.

8. The method of claim 1, wherein the test compound of (b) is a compound fragment.

9. The method of claim 1, wherein the compound is an allosteric inducer or inhibitor of a target protein or fragment thereof.

10. The method of claim 1, wherein the assay to assess binding is a non-competitive assay.

11. The method of claim 1, wherein evaluation of test compound binding is performed by surface plasmon resonance, comprising BIAcore analysis.

12. The method of claim 1, further comprising a step of generating three-dimensional structural information, wherein the step of generating three-dimensional structural information comprise X-ray crystallography between step (c) and step (d), or following step (d) to gain structural information on binding of a test compound.

13. The method of claim 1, wherein the method comprises repeating steps (b) and (c) in the presence of a protein-construct wherein a first test compound is bound.

14. The method of claim 1, wherein the method comprises repeating steps (b) and (c) in the presence of a protein-construct wherein a first test compound and a second test compound are bound.

15. The method of claim 1, wherein each antibody or fragment thereof obtained in step (a) is selected from the group consisting of a complete antibody, a Fab, a modified a Fab, a Fab', Fv, VH, VL, VHH and an IgNAR V domain.

16. The method of claim 1, wherein two or more different antibodies are employed in step (a) to each bind a different molecule of protein with the same amino sequence, comprising providing the antibody constrained proteins in an array.

17. The method according to claim 16, wherein the protein molecules constrained by the two or more different antibodies are screened concomitantly with the same compound library.

18. The method of claim 1, wherein the method is performed in a liquid phase.

19. The method according to claim 18, wherein after relevant binding interactions have taken place, the protein-complex and, optionally, any test compound bound thereto are bound to a solid phase, suitable for use high-throughput screening, wherein the solid phase comprises a plate.

20. The method according to claim 19, wherein the complex is captured on the solid phase coated with a reagent that recognises a marker or a tag in the complex, wherein the tag is a his tag, a flag tag or an Fc region of an antibody.

21. The method of claim 1, wherein the functionally modifying antibody or a combination thereof are coated onto a solid phase pre or post binding to the protein of interest or fragment thereof and prior to screening with a test compound.

22. The method of claim 1, wherein step (c) further comprises evaluating whether the test compound of step b) binds the protein or fragment in the absence of antibody and step (d) further comprises selecting a compound from step (c) based on the ability of the test compound to only bind the antibody-constrained protein or fragment and not the unconstrained protein or fragment.

23. The method of claim 1, wherein the protein of interest is human IgE.

* * * * *